US008579177B2

(12) United States Patent
Beetel

(10) Patent No.: US 8,579,177 B2
(45) Date of Patent: *Nov. 12, 2013

(54) SURGICAL INSTRUMENTS EMPLOYING SENSORS

(75) Inventor: Robert J. Beetel, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/468,229

(22) Filed: May 10, 2012

(65) Prior Publication Data

US 2012/0217282 A1      Aug. 30, 2012

Related U.S. Application Data

(60) Continuation of application No. 13/191,579, filed on Jul. 27, 2011, now Pat. No. 8,181,839, which is a continuation of application No. 12/760,635, filed on Apr. 15, 2010, now Pat. No. 8,002,795, which is a division of application No. 11/444,548, filed on May 31, 2006, now Pat. No. 7,717,312.

(60) Provisional application No. 60/687,243, filed on Jun. 3, 2005, provisional application No. 60/687,214, filed on Jun. 3, 2005.

(51) Int. Cl.
*A61B 17/068* (2006.01)

(52) U.S. Cl.
USPC ....... 227/175.1; 227/19; 227/176.1; 227/180; 606/139; 606/219

(58) Field of Classification Search
USPC .............. 227/19, 175.1, 176.1, 175.2, 178.1, 227/180.1; 606/139, 219
See application file for complete search history.

(56) References Cited

U.S. PATENT DOCUMENTS

| 5,258,007 | A | 11/1993 | Spetzler et al. |
| 5,383,880 | A | 1/1995 | Hooven |
| 5,403,312 | A | 4/1995 | Yates et al. |

(Continued)

FOREIGN PATENT DOCUMENTS

| EP | 0552050 A2 | 7/1993 |
| EP | 0552050 B1 | 7/1993 |

(Continued)

OTHER PUBLICATIONS

International Extended Search Report corresponding to European Application EP 06 01 1501.1, completed Sep. 21, 2006 and mailed Dec. 12, 2006; 3 pages.

(Continued)

*Primary Examiner* — Scott A. Smith

(57) ABSTRACT

According to an aspect of the present disclosure, a surgical instrument for operating on tissue is provided. The surgical instrument includes an end effector including a first tissue engaging member and a second tissue engaging member in juxtaposed relation to the first tissue engaging member; a gap determination element operatively associated with each of the first tissue engaging member and the second tissue engaging member for measuring a gap distance between the first tissue engaging member and the second tissue engaging member; and a tissue contact determining element operatively associated with a respective tissue contacting surface of at least one of the first tissue engaging member and the second tissue engaging member. The present disclosure also relates to methods of using the surgical instrument.

19 Claims, 19 Drawing Sheets

(56) References Cited

U.S. PATENT DOCUMENTS

| | | | |
|---|---|---|---|
| 5,464,144 A | 11/1995 | Guy et al. |
| 5,503,320 A | 4/1996 | Webster et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,937 A | 7/1996 | Boiarski et al. |
| 5,558,671 A | 9/1996 | Yates |
| 5,562,239 A | 10/1996 | Boiarski et al. |
| 5,609,607 A | 3/1997 | Hechtenberg et al. |
| 5,665,085 A | 9/1997 | Nardella |
| 5,713,896 A | 2/1998 | Nardella |
| 5,735,848 A | 4/1998 | Yates et al. |
| 5,782,397 A | 7/1998 | Koukline |
| 5,964,394 A | 10/1999 | Robertson |
| 5,965,880 A | 10/1999 | Wolf et al. |
| H1904 H | 10/2000 | Yates et al. |
| 6,221,023 B1 | 4/2001 | Matsuba et al. |
| H2037 H | 7/2002 | Yates et al. |
| 6,436,097 B1 | 8/2002 | Nardella |
| 6,436,107 B1 | 8/2002 | Wang et al. |
| 6,602,252 B2 | 8/2003 | Mollenauer |
| 6,716,233 B1 | 4/2004 | Whitman |
| 6,817,508 B1 | 11/2004 | Racenet et al. |
| 7,300,450 B2 | 11/2007 | Vleugels et al. |
| 7,717,312 B2 | 5/2010 | Beetel |
| 8,002,795 B2 | 8/2011 | Beetel |
| 8,181,839 B2 * | 5/2012 | Beetel ........................ 227/175.1 |
| 2004/0153124 A1 | 8/2004 | Whitman |
| 2004/0232201 A1 | 11/2004 | Wenchell et al. |
| 2005/0067458 A1 | 3/2005 | Swayze et al. |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0131390 A1 | 6/2005 | Heinrich et al. |
| 2006/0097025 A1 | 5/2006 | Milliman et al. |
| 2006/0271094 A1 | 11/2006 | Hudson et al. |

FOREIGN PATENT DOCUMENTS

| | | |
|---|---|---|
| EP | 1813206 A1 | 8/2007 |
| WO | WO-98/30153 A1 | 7/1998 |
| WO | WO-03/020139 A2 | 3/2003 |
| WO | WO-03/020139 A3 | 3/2003 |
| WO | WO-03/090630 A2 | 11/2003 |
| WO | WO-03/090630 A3 | 11/2003 |

OTHER PUBLICATIONS

International Search Report corresponding to European Application EP 10 25 1306, completed Dec. 2, 2010; 2 pages.

* cited by examiner

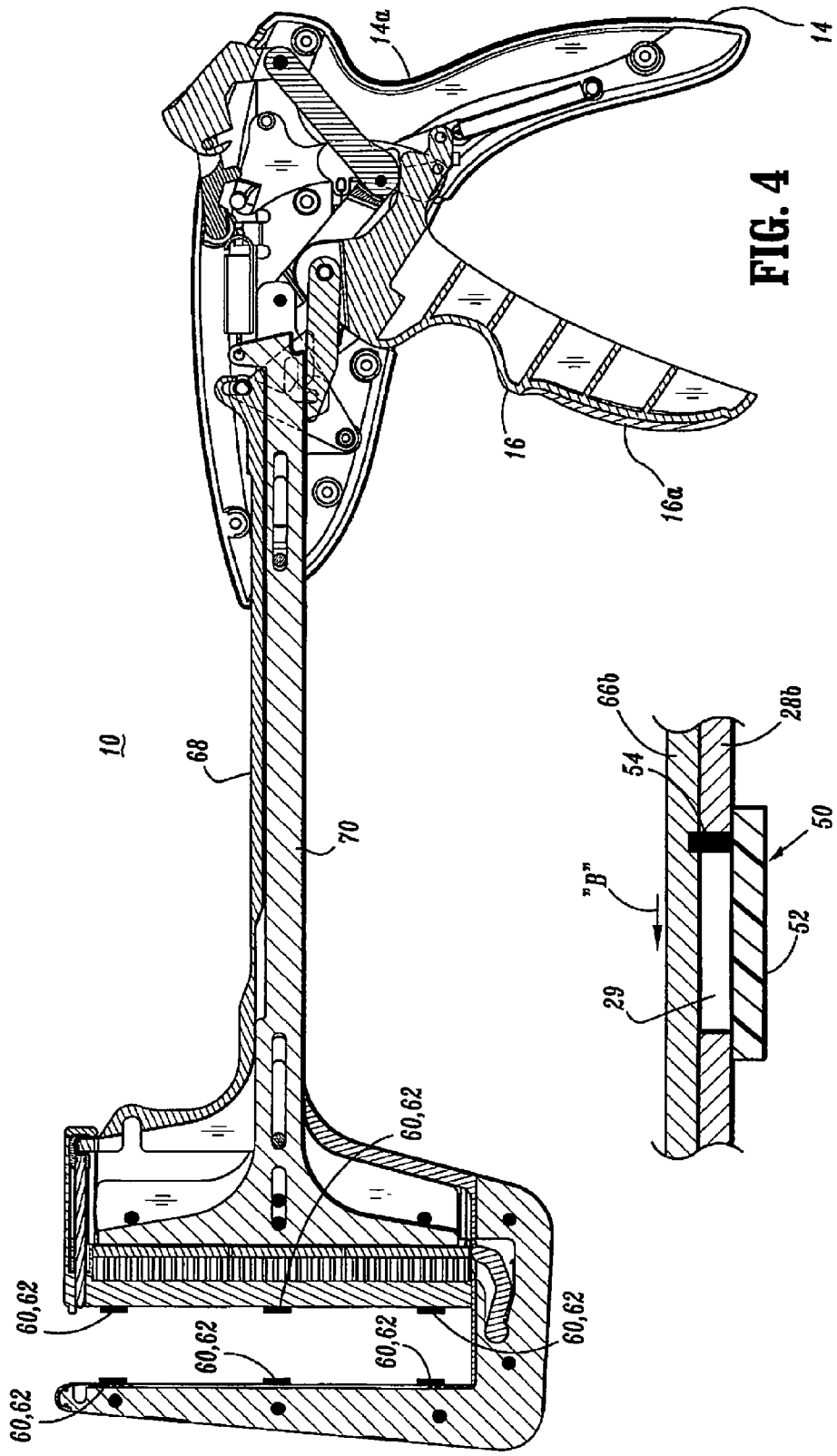

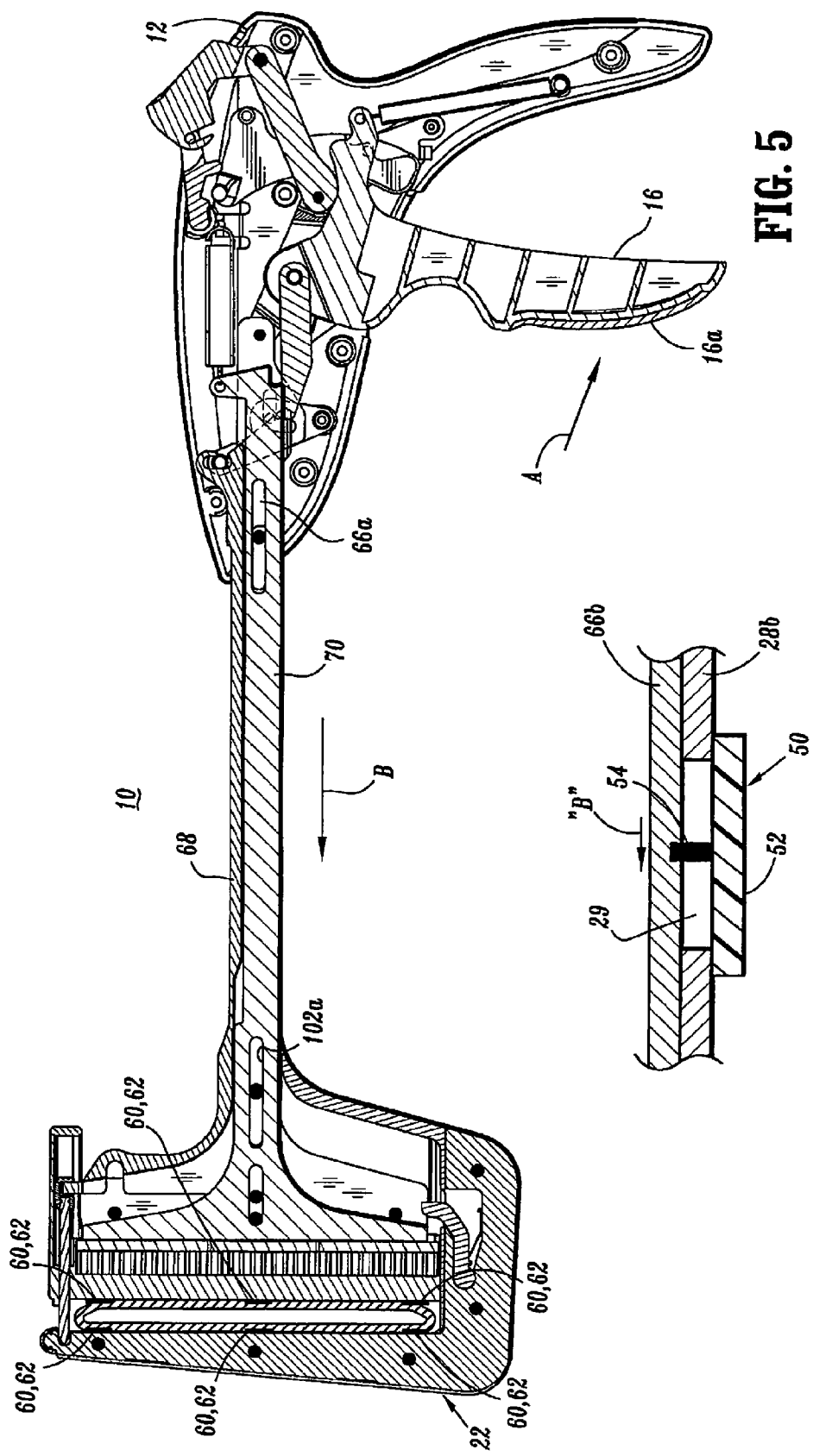

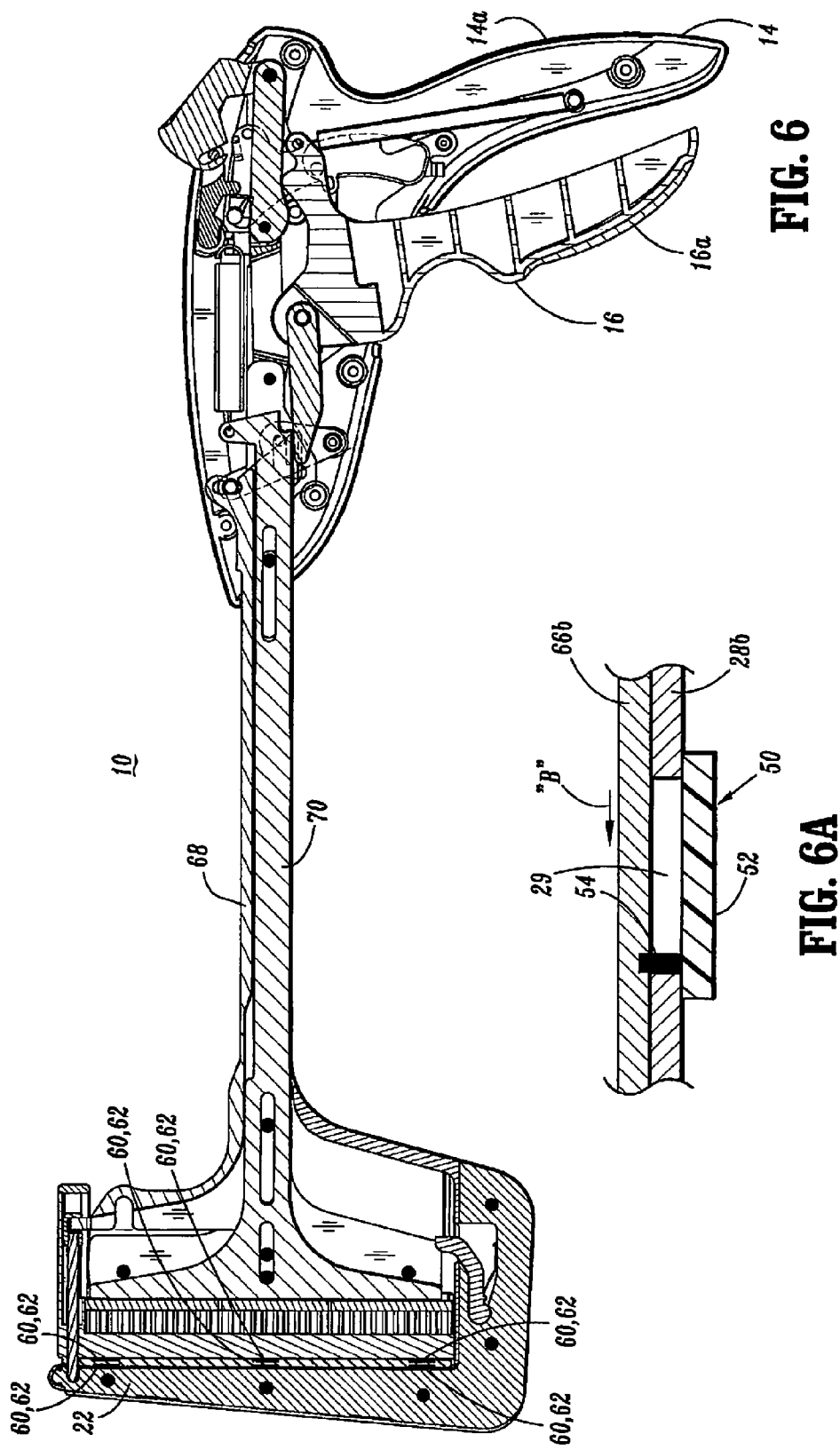

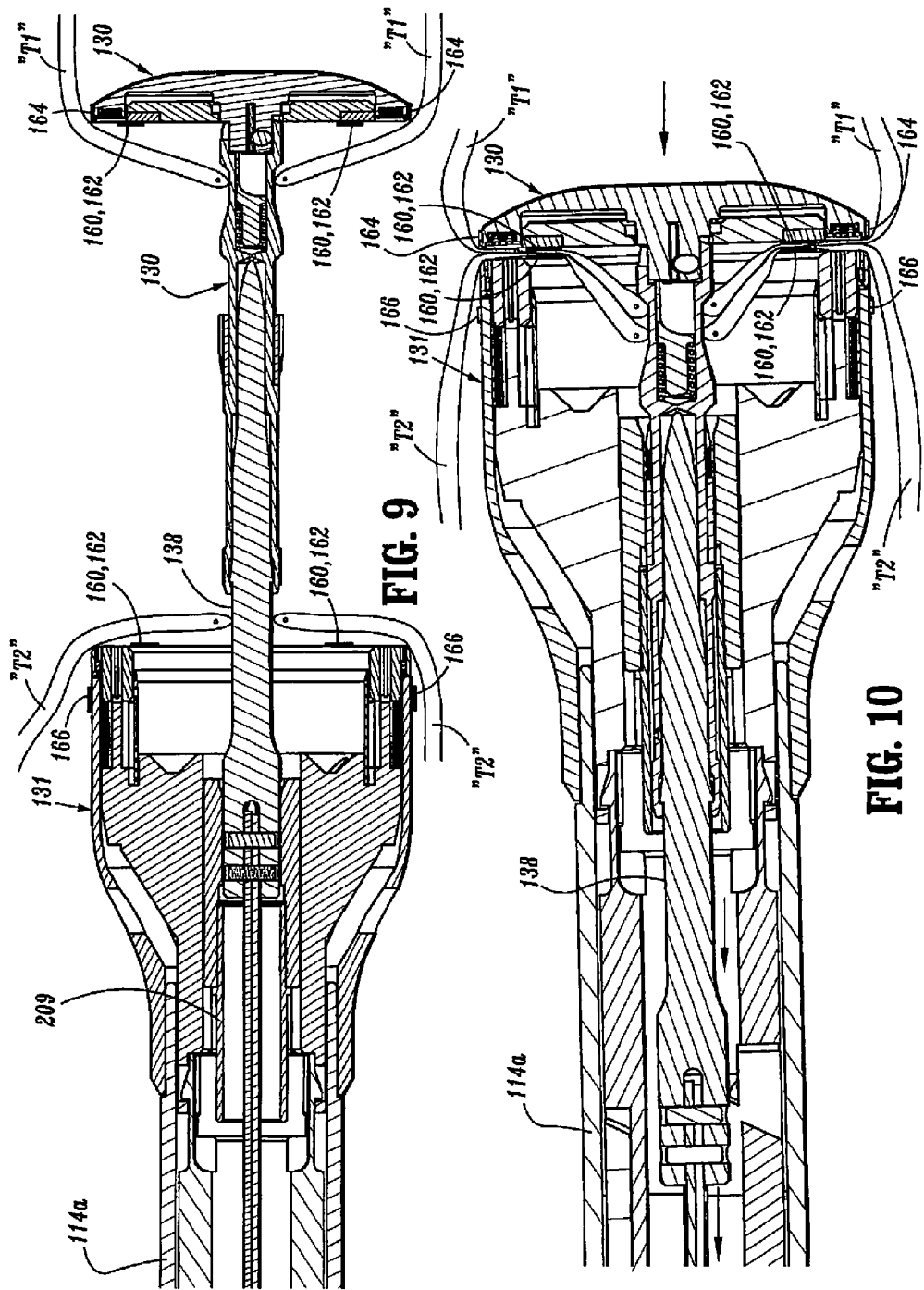

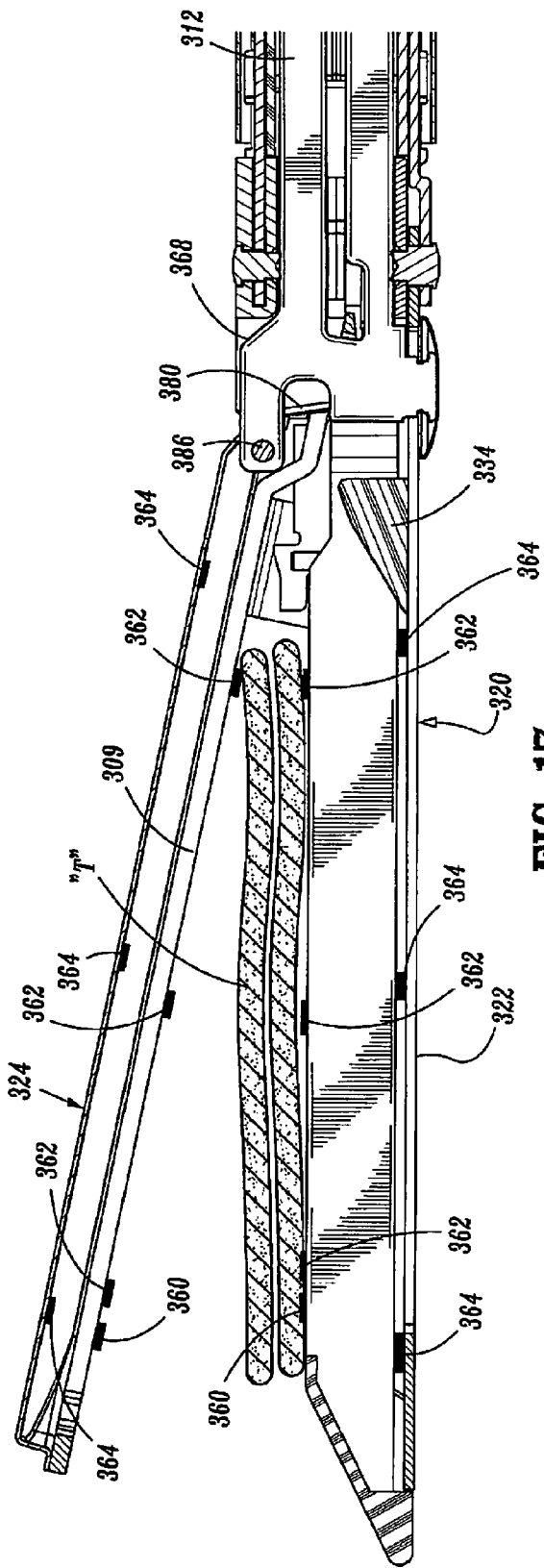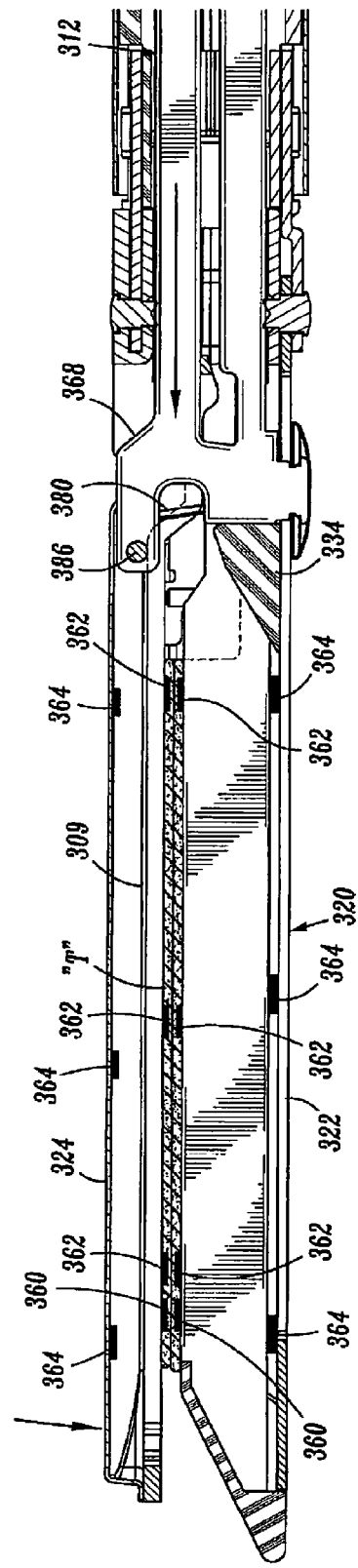
FIG. 17
FIG. 18

SURGICAL INSTRUMENTS EMPLOYING SENSORS

CROSS-REFERENCE TO RELATED APPLICATIONS

The present application is a Continuation application which claims the benefit of and priority to U.S. patent application Ser. No. 13/191,579 (U.S. Patent Application Publication No. 2011/0282329), filed Jul. 27, 2011 now U.S. Pat. No. 8,181,839, which is a Continuation application which claims the benefit of and priority to U.S. patent application Ser. No. 12/760,635, filed Apr. 15, 2010 (U.S. Pat. No. 8,002,795), which is a Divisional application which claims the benefit of and priority to U.S. patent application Ser. No. 11/444,548, filed May 31, 2006 (U.S. Pat. No. 7,717,312), which claims the benefit of and priority to each of U.S. Provisional Application No. 60/687,243, filed Jun. 3, 2005, and U.S. Provisional Patent Application Ser. No. 60/687,214, filed on Jun. 3, 2005, the entire contents of each of which being incorporated herein by reference.

BACKGROUND

1. Technical Field

The present disclosure relates to surgical instruments and, more particularly, to mechanical, electro-mechanical and energy-based surgical instruments and systems.

2. Background of Related Art

Surgical instruments used in open and minimally invasive surgery are limited in their ability to sense and/or control conditions and/or parameters and factors critical to effective operation. For example, conventional surgical instruments cannot measurably detect the amount of tissue positioned between tissue contacting surfaces of an end effector of the surgical instrument, the clamping force being exerted on the tissue, the distance between juxtaposed tissue contacting surfaces, and/or the viability of the tissue clamped therebetween.

Accordingly, a need exists for surgical instruments and/or systems that can sense a multitude of parameters and factors at the target surgical site, such as, for example, the distance between juxtaposed tissue contacting surfaces of the surgical instrument, the amount of tissue positioned between tissue contacting surfaces of an end effector of the surgical instrument, the clamping force being exerted on the tissue, and/or the viability of the tissue clamped therebetween.

A need exists for surgical instruments and/or systems which can, according to the conditions sensed and/or measured at the target surgical site, utilize, display, record and/or automatically control the position of the tissue contacting surfaces of the surgical instrument and/or system, alert a surgeon prior to operation of the surgical instrument and/or system, and/or operate the surgical instrument and/or system.

SUMMARY

According to an aspect of the present disclosure, a surgical instrument for operating on tissue is provided. The surgical instrument includes an end effector including a first tissue engaging member and a second tissue engaging member in juxtaposed relation to the first tissue engaging member; a gap determination element operatively associated with each of the first tissue engaging member and the second tissue engaging member for measuring a gap distance between the first tissue engaging member and the second tissue engaging member; and a tissue contact determining element operatively associated with a respective tissue contacting surface of at least one of the first tissue engaging member and the second tissue engaging member.

The surgical instrument may further include a processor operatively connected to the gap determination element and to each of the tissue contact determining elements. Each of the first and second tissue engaging elements includes at least one tissue contact determining element supported on the tissue contacting surface thereof.

The gap determination element may be selected from the group consisting of a slide potentiometer, a rotational potentiometer, a linear variable differential transformer, a magneto-resistive element, capacitive elements, electromagnetic induction sensors, Hall effect sensors, and optical based sensors.

The tissue contact determining element may be selected from the group consisting of pressure sensors, electrical contacts and sensing circuits, force transducers, piezoelectric elements, piezoresistive elements, metal film strain gauges, semiconductor strain gauges, inductive pressure sensors, capacitive pressure sensors, and potentiometric pressure transducers.

The surgical instrument may be a stapler.

The tissue contact determining element may transmit a signal to the processor when a tissue is positioned between the first and second tissue engaging elements and when the tissue contacting surface of each of the first and second tissue engaging elements contacts the tissue. The signal transmitted to the processor, when the tissue contacting surface of each of the first and second tissue engaging elements contacts the tissue, may be the initial tissue thickness.

The processor may be configured to monitor at least one of a compression force and a strain on the tissue as the tissue is compressed between the first and second tissue engaging members. The processor may be configured to activate a signal when at least one of the compression force and strain on the tissue achieves a predetermined level of compression or strain. The processor may also be configured to activate a signal when a tissue contact determining element engages at least one of a first and second tissue.

The predetermined level of compression or strain on the tissue is maintained in a data look-up table. The data look-up table may include predetermined levels of compression or strain for numerous tissue types. The predetermined level of compression or strain may be a percentage of the initial tissue thickness.

According to another aspect of the present disclosure, a method of performing a surgical procedure on tissue is provided. The method includes the steps of providing a surgical instrument including an end effector including a first tissue engaging member and a second tissue engaging member in juxtaposed relation to the first tissue engaging member; positioning the first and second tissue engaging members on opposite sides of the tissue; approximating the first and second tissue engaging members until the tissue contact determining element is engaged; recording an initial distance between the first and second tissue engaging members as an initial tissue thickness; further approximating the first and second tissue engaging members to compress the tissue therebetween; monitoring at least one of a compression force and a strain on the tissue; and terminating the approximation of the first and second tissue engaging members when at least one of the compression force and the strain on the tissue reaches a predetermined level.

The surgical instrument may include a gap determination element operatively associated with each of the first tissue engaging member and the second tissue engaging member for measuring a gap distance between the first tissue engaging member and the second tissue engaging member; and a tissue contact determining element operatively associated with a respective tissue contacting surface of at least one of the first tissue engaging member and the second tissue engaging member.

The surgical instrument may further include a processor operatively connected to each of the gap determining elements and tissue contact determining elements. The tissue contact determining elements may transmit a signal to the processor when the first and second tissue engaging members are in contact with the tissue. The gap determining elements may transmit signals to the processor regarding a distance between the first and second tissue engaging members.

The method may further include the step of determining at least one of the compression force and strain on the tissue as a result of the reduction in distance between the first and second tissue engaging members.

The method may further include the step of activating an indicator when at least one of the compression force and strain on the tissue achieves the predetermined level of compression or strain. The method may still further include the step of setting the predetermined level of compression or strain for the tissue prior to the compression of the tissue.

The surgical instrument may be a stapler.

The method may further include the step of firing the surgical stapler when at least one of the compression force and the strain on the tissue is approximately equal to the predetermined level of compression or strain.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 4 is a side, longitudinal cross-sectional view of the surgical instrument of FIG. 1, shown in a first condition;

FIG. 4A is an enlarged schematic illustration of a position sensor of the surgical instrument of FIG. 1, shown in a first condition;

FIG. 5 is a side, longitudinal cross-sectional view of the surgical instrument of FIG. 1, shown in a second condition;

FIG. 5A is an enlarged schematic illustration of the position sensor of the surgical instrument of FIG. 1, shown in a second condition;

FIG. 6 is a side, longitudinal cross-sectional view of the surgical instrument of FIG. 1, shown in a third condition;

FIG. 6A is an enlarged schematic illustration of the position sensor of the surgical instrument of FIG. 1, shown in a third condition;

FIG. 9 is a side cross-sectional view of the distal end of the surgical instrument of FIGS. 7 and 8, shown in a first condition;

FIG. 10 is a side cross-sectional view of the distal end of the surgical instrument of FIGS. 7 and 8, shown in a second condition;

FIG. 17 is an enlarged, side cross-sectional view of a tool assembly of the surgical instrument of FIGS. 15 and 16, shown in the first, unapproximated condition;

FIG. 18 is an enlarged, side cross-sectional view of a tool assembly of the surgical instrument of FIGS. 15 and 16, shown in a second, approximated condition;

DETAILED DESCRIPTION OF EMBODIMENTS

Figure 1:
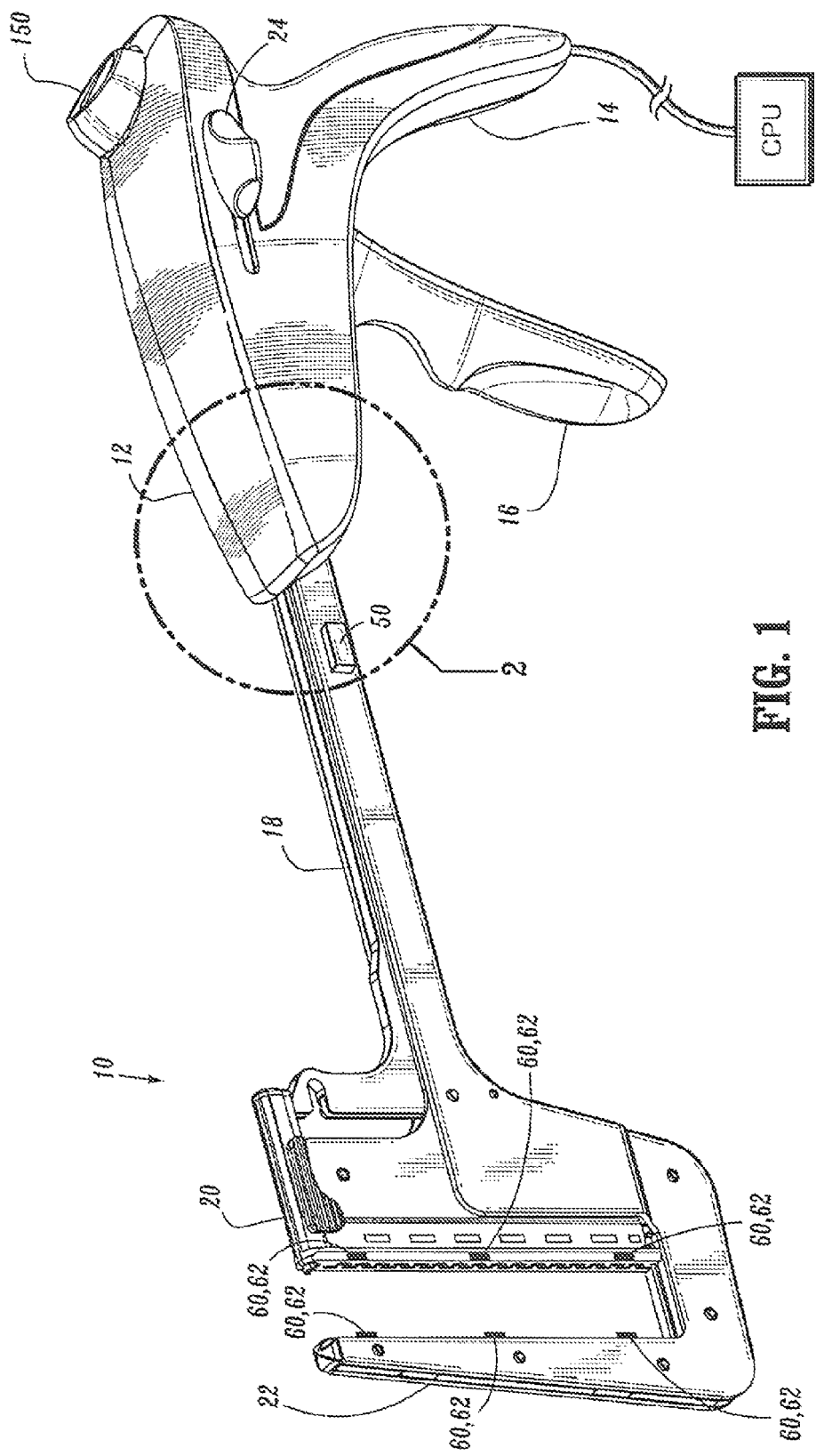
FIG. 1 is a perspective view of a surgical instrument according to an embodiment of the present disclosure.

Preferred embodiments of the presently disclosed surgical instruments and systems will now be described in detail with reference to the drawing figures wherein like reference numerals identify similar or identical elements. As used herein and as is traditional, the term "distal" will refer to that portion which is further from the user while the term "proximal" will refer to that portion which is closer to the user.

A surgical instrument in accordance with an embodiment of the present disclosure is shown generally as 10 in FIGS. 1-6A. Surgical instrument 10 includes a body 12 defining a stationary handle 14, a pivotable trigger 16, an elongated central body portion 18, and an end effector including a first member or cartridge assembly 20 and a second member of anvil assembly 22. A thumb button 24 is slidably positioned on each side of body 12. Thumb buttons 24 are movable to manually advance an alignment pin assembly (not shown). A release button 150 is positioned on the proximal end of body 12 and is depressible to allow cartridge assembly 20 to return from an approximated position disposed adjacent to anvil assembly 22 to a position spaced from anvil assembly 22 (as shown).

Figure 2:
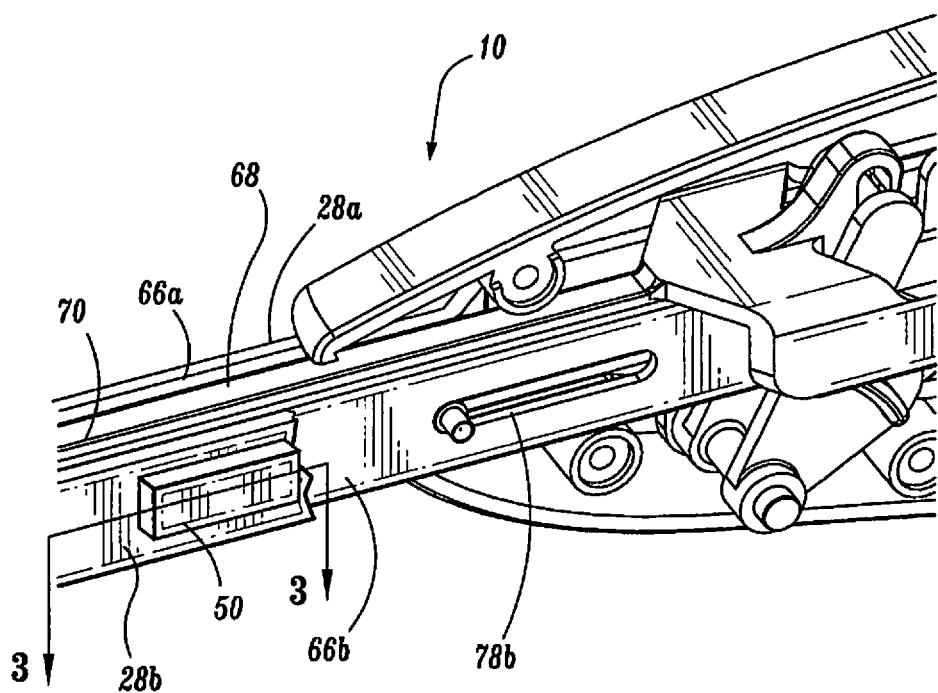
FIG. 2 is an enlarged perspective view, partially cut away, of the indicated area of detail of FIG. 1.

Referring to FIG. 2, surgical stapling instrument 10 includes a pair of clamp slide members 66a and 66b, an alignment pin pusher 68 slidably interposed between clamp slide members 66a and 66b, and a thrust bar 70 slidably interposed between alignment pin pusher 68 and clamp slide member 66b. Clamp slide members 66a and 66b, alignment pin pusher 68 and thrust bar 70 are slidably supported between frame members 28a and 28b for movement between retracted and advanced positions in response to movement of trigger 16 through an approximation stroke and/or a firing stroke.

As seen in FIGS. 1 and 2, a gap measurement element or device 50 is operatively supported on frame member 28b. In particular, gap measurement device 50 is secured to frame member 28b. Gap measurement device 50 is configured and adapted to measure and convey to the user the distance between cartridge assembly 20 and anvil assembly 22 during the surgical procedure.

Figure 3:
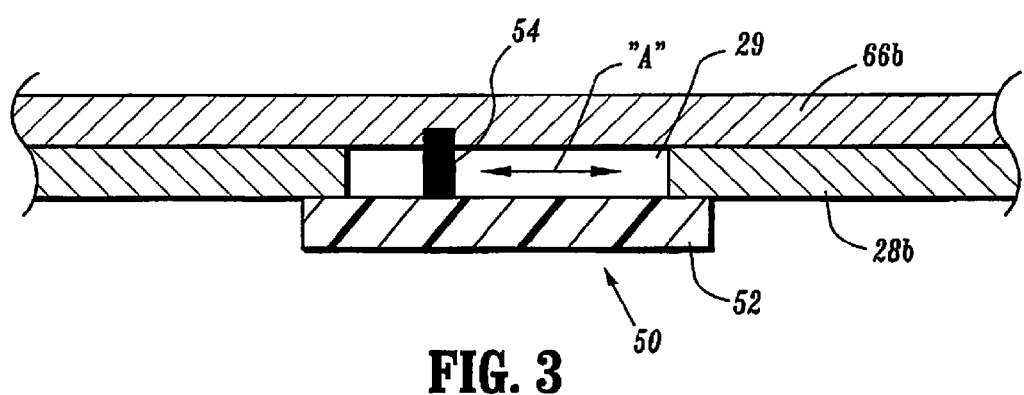
FIG. 3 is a schematic cross-sectional view as taken along section lines 3-3 of FIG. 2.

Gap measurement device 50 may be, for example, a slide potentiometer, a rotational potentiometer (see FIG. 3A), or the like. As best seen in FIG. 3, gap measurement device 50 includes a body portion 52 secured to a surface of frame member 28b and a wiper 54, extending through an elongate slot 29 formed in frame member 28b, operatively connected to clamp slide member 66b. Wiper 54 is slidably supported in body portion 52 such that as wiper 54 moves along the length of body portion 52 (in the direction of double-headed arrow "B") a different impedance is created and thus a different current (or voltage) may be transmitted to a control unit (not shown). Wiper 54 is desirably fixedly connected to clamp slide member 66b. In this manner, as clamp slide member 66b is axially displaced with respect to frame member 28b, wiper 54 is axially displaced with respect to body portion 52, thereby altering and/or changing the impedance value of gap measurement device 50.

Figure 3A:
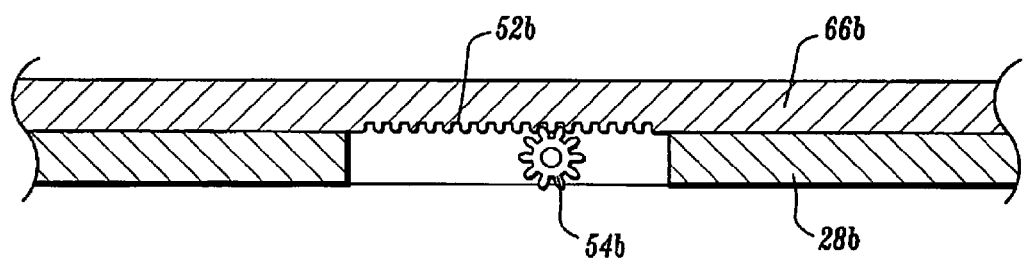
FIG. 3A s a schematic cross-sectional view as taken along section lines 3-3 of FIG. 2, illustrating an alternate embodiment of the present disclosure.

As seen in FIG. 3A, the gap measurement device 50 may be in the form of a rotational potentiometer including a gear or pinion 54a operatively supported on frame member 28b and a rack 52b or the like formed in/on or supported on clamp slide member 66b, wherein pinion 54b is operatively engaged with rack 52b. In operation, as clamp slide member 66b moves, proximally or distally, relative to frame member 28b rack 52b causes pinion 54b to rotate clockwise or counter-clockwise thereby varying the current or voltage.

Operation of surgical instrument 10 will now be described with reference to FIGS. 4-6A. It is noted that the movements of the various components of surgical instrument 10 will be described from the vantage point of one viewing the instrument as positioned in the referenced FIG.

FIGS. 4 and 4A illustrate surgical instrument 10 prior to use. As illustrated, cartridge assembly 60 and anvil assembly 62 are in spaced relation, trigger 16 is in the non-compressed position, and clamp slides 66a and 66b and thrust bar 70 are in the retracted position. When clamp slide 66b is in the retracted position, wiper 54 of gap measurement device 50 is positioned rearwardly within slot 29 of frame member 28b. With wiper 54 of gap measurement device 50 in the retracted position, a unique voltage is generated and measured by a processor (not shown) which indicates to the processor that cartridge assembly 60 and anvil assembly 62 are in spaced relation to one another.

FIGS. 5 and 5A illustrate surgical instrument 10 during the approximation stroke of trigger 16. As illustrated, trigger 16 is moved in the direction indicated by arrow "A" to effectively move front link 112 forwardly and to move clamp slides 66a and 66b forwardly through pin 88. As seen in FIG. 5A, as clamp slide 66b is moved forwardly, wiper 54 of gap measurement device 50 is also moved forwardly relative to body portion 52, thereby varying the voltage generated by gap measurement device 50. As wiper 54 of gap measurement device 50 is moved forwardly relative to body portion 52, thereby varying the voltage generated and measured by the processor, the distance between cartridge assembly 20 and anvil assembly 22 may be determined.

FIGS. 6 and 6A illustrate surgical instrument 10 in the fully approximated position with trigger 16 in the compressed position. As illustrated, trigger 16 has been fully approximated, thereby fully advancing clamp slides 66a and 66b such that cartridge assembly 20 and anvil assembly 22 are in the approximated position. Concomitantly therewith, wiper 54 of gap measurement device 50 is advanced to a forward most position within slot 29 of frame member 28b. With wiper 54 of gap measurement device 50 in a distal-most position, a unique voltage is generated and measured by the processor which indicates to the processor that cartridge assembly 20 and anvil assembly 22 are in the approximated position.

Turning now to FIGS. 1 and 4-6A, surgical instrument 10 includes a plurality of contact sensors 60 placed along the length of a tissue contacting surface of each of cartridge assembly 20 and anvil assembly 22. Contact sensors 60 are connected to the processor or CPU and provide indication as to when an object, such as, tissue, is located between cartridge assembly 20 and anvil assembly 22 and in contact therewith. Contact sensors 60 function to determine an initial thickness of the tissue interposed between cartridge assembly 20 and anvil assembly 22. This initial tissue thickness defines a zero point of reference.

According to a method of operation, with cartridge assembly 20 and anvil assembly 22 in spaced relation to one another, target tissue is placed therebetween. With the target tissue positioned between cartridge assembly 20 and anvil assembly 22, cartridge assembly 20 and anvil assembly 22 are approximated towards one another until the target tissue makes contact with the contact sensors 60. At this time, the distance between cartridge assembly 20 and anvil assembly 22 is measured and/or recorded. This initial distance between cartridge assembly 20 and anvil assembly 22 is recorded as the initial thickness of the tissue or the zero point of reference. With the contact distance between cartridge assembly 20 and anvil assembly 22 or the initial tissue thickness recorded, the cartridge assembly 20 and the anvil assembly 22 are further approximated until a desired gap between the cartridge assembly 20 and the anvil assembly 22 is obtained. Once the desired gap between the cartridge assembly 20 and the anvil assembly 22 is achieved, this distance is recorded as the compressed tissue thickness.

Alternatively, following the determination of the initial thickness of the tissue, a predetermined value for the compression and/or strain of the tissue may be set on the processor or CPU. The predetermined value of the compression and/or strain may be obtained from a data look-up table or the like for the particular tissue being compressed. Accordingly, as the cartridge assembly 20 and the anvil assembly 22 are approximated toward one another, thereby reducing the gap therebetween, the compression and/or strain of the tissue is continually monitored until the compression and/or strain on the tissue achieves the predetermined value. At such a time, a sensor indicator may be activated (e.g., a light, a tone, etc.) to advise the user that the predetermined value for the compression and/or strain has been achieved.

According to the present disclosure, it has been discovered that an excessive amount of compression or strain on the tissue may result in the tissue having insufficient blood flow thereto in order to achieve an acceptable hemostasis and/or tissue fusion. An insufficient flow of blood to the tissue may result in tissue necrosis or the like. Additionally, it has been discovered that an insufficient amount of compression or strain on the tissue may result in the tissue having too much blood flow thereto in order to achieve an acceptable hemostasis and/or tissue fusion. Too much blood flow to the tissue may result in the tissue "bleeding out".

The recorded compression or strain of the tissue is compared to an existing record or data look-up table of acceptable tissue compressions and/or strains for different tissues. The gap between the cartridge assembly 20 and the anvil assembly 22 is adjusted until the compression and/or strain on the tissue is within an acceptable range.

Once the desired strain on the tissue is achieved, surgical instrument 10 is fired using either a universal-type staple or staples appropriately sized for the thickness of the tissue clamped therebetween. The strain on the tissue is determined using known formulas based upon initial/compressed tissue thickness. Reference may be made to U.S. application Ser. No. 11/409,154, filed on Apr. 21, 2006, the entire content of which is incorporated herein by reference, for a more detailed discussion of the determination of strain on tissue.

Reference may be made to U.S. Pat. No. 6,817,508, the entire content of which is incorporated herein by reference, for a more detailed discussion of the structure and operation of surgical instrument 10.

Figure 7:
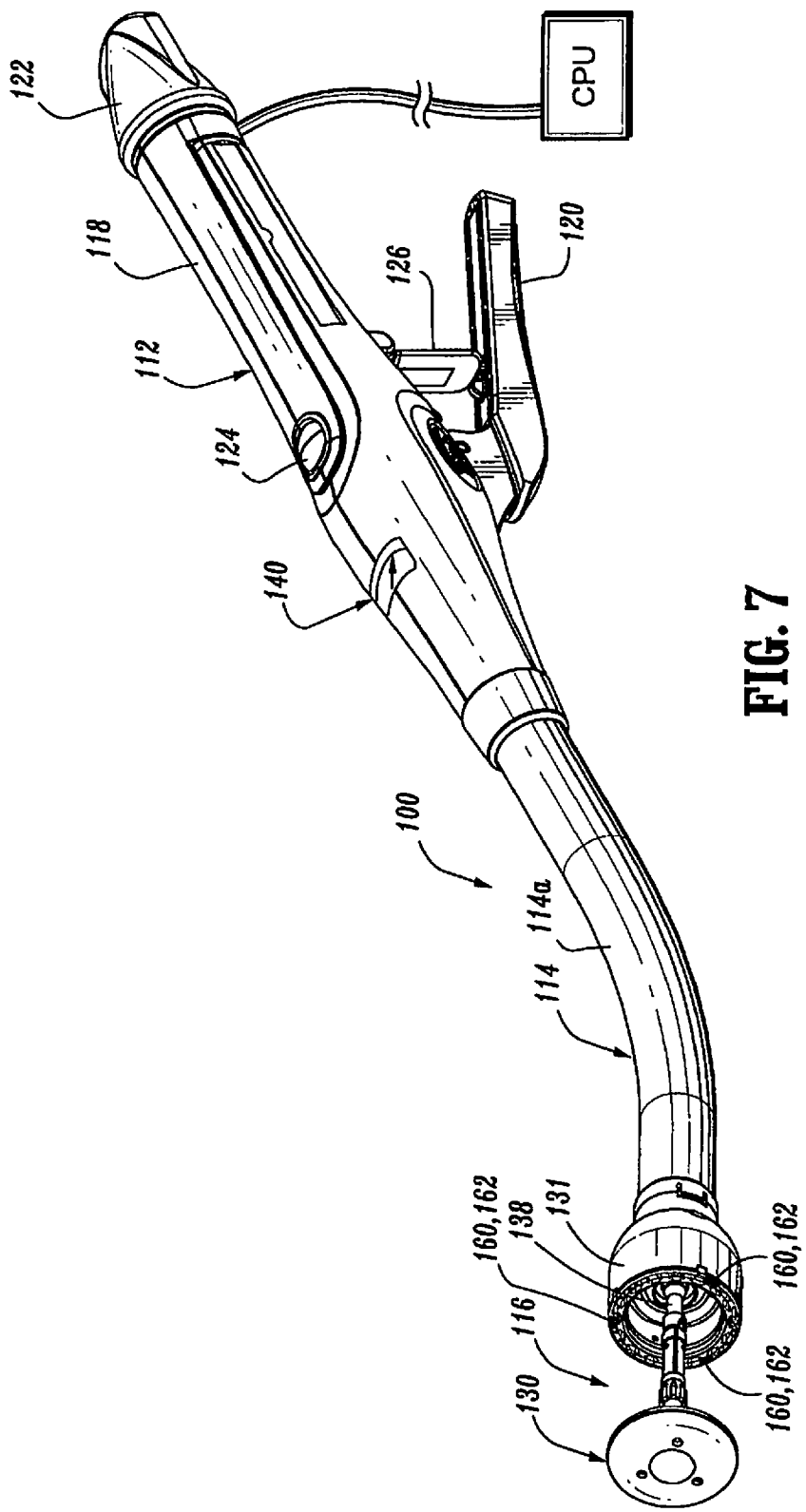
FIG. 7 is a perspective view of a surgical instrument according to another embodiment of the present disclosure.

Turning now to FIGS. 7-11, a surgical instrument according to another embodiment of the present disclosure is generally designated as 100. As seen in FIG. 7, surgical instrument 100 includes a proximal handle assembly 112, an elongated central body portion 114 including a curved elongated outer tube 114a, and a distal head portion 116. Alternately, in some surgical procedures, e.g., the treatment of hemorrhoids, it is desirable to have a substantially straight, preferably shortened, central body portion. The length, shape and/or the diameter of body portion 114 and head portion 116 may also be varied to suit a particular surgical procedure.

Handle assembly 112 includes a stationary handle 118, a firing trigger 120, a rotatable approximation knob 122 and an indicator 124. Stationary handle 118 defines a housing for the internal components of handle assembly 112. The internal components of handle portion 112 will be discussed in detail below. Preferably, cushioned and/or resilient slip resistant portions such as a grip (not shown) can be fastened to or included as part of stationary handle 118 and firing trigger 120. A pivotally mounted trigger lock 126 is fastened to handle assembly 112 and is manually positioned to prevent inadvertent firing of surgical instrument 100. Indicator 124 is positioned on the stationary handle 118 and includes indicia, e.g., color coding, alpha-numeric labeling, etc., to identify to a surgeon whether the device is approximated and is ready to be fired. Head portion 116 includes an anvil assembly 130 and a shell assembly 131. Each of these assemblies will be discussed in detail below.

Figure 8:
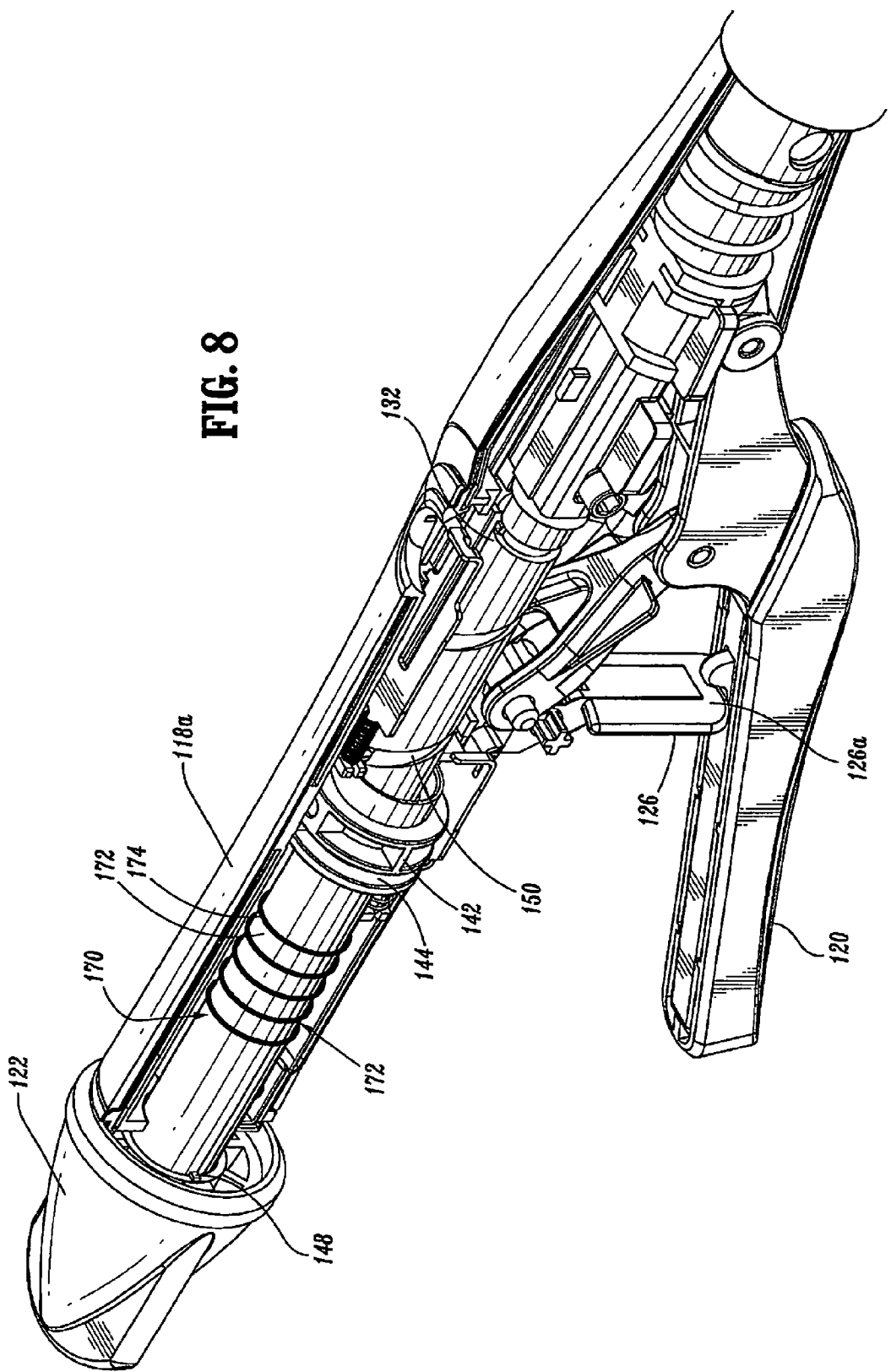
FIG. 8 is a top perspective view of the top of the handle assembly of the surgical instrument of FIG. 7 with a handle section removed therefrom.

Turning now to FIG. 8, the internal components of handle assembly 112 include and are not limited to the proximal components of an approximation and firing mechanism, a firing lockout mechanism and an indicator drive mechanism.

Referring to FIG. 8, the approximation mechanism includes approximation knob 122, a drive screw 132, a rotatable sleeve 133, and an anvil retainer 138 (see FIG. 7) for supporting an anvil assembly 130. Rotatable sleeve 133 includes a substantially cylindrical hollow body portion 140 and a substantially cylindrical collar 142 which together define a central bore. Collar 142 has an annular groove 144 formed thereabout which is dimensioned to receive an inwardly extending flange formed on an inner wall of handle assembly 118. Engagement between groove 144 and the flanges axially fixes sleeve 133 within handle assembly 118 while permitting rotation of sleeve 133 in relation to handle assembly 118. A pair of diametrically opposed elongated ribs 148 are positioned or formed on the outer surface of body portion 140. Approximation knob 122 includes a pair of internal slots (not shown) positioned to receive ribs 148 of sleeve 133 to rotatably fix sleeve 133 to knob 122, such that rotation of knob 122 causes concurrent rotation of sleeve 133.

The proximal half of screw 132 includes a helical channel 150 and is dimensioned to be slidably positioned within the central bore of rotatable sleeve 133. Since sleeve 133 is axially fixed with respect to handle assembly 118, rotation of sleeve 133 about screw 132 causes a pin (not shown) to move along channel 150 of screw 132 to effect axial movement of screw 132 within handle assembly 118.

In operation, when approximation knob 122 is manually rotated, rotatable sleeve 133 is rotated about the proximal end of screw 132 to move a pin along helical channel 150 of screw 132. Since sleeve 133 is axially fixed to handle assembly 118, as the pin is moved through channel 150, screw 132 is advanced or retracted within handle assembly 118. As a result, top and bottom screw extensions (not shown), which are fastened to the distal end of screw 132, and to anvil retainer 138, are moved axially within elongated body portion 114. Since anvil assembly 130 is secured to the distal end of anvil retainer 138, rotation of approximation knob 122 will effect movement of anvil assembly 130 in relation to shell assembly 131 between spaced and approximated positions.

With continued reference to FIG. 8, an LVDT 170 (Linear Variable Differential Transformer) is provided in handle assembly 118 for determining a gap distance between anvil assembly 130 and shell assembly 131. In particular, LVDT 170 may include a coil 174 disposed within rotatable sleeve 133 and a magnet core 172 may be placed within coil 174. Generally, as magnet core 172 moves back through the collar/handle assembly 118 the magnet core 172 gets closer/further to/from coil 174 and produces an electrical output. In one embodiment, magnet core 172 may include a screw having a magnet supported thereon or therein.

In operation, as approximation knob 122 is rotated to approximate anvil assembly 130 towards shell assembly 131, LVDT 170 functions to measure and determine the distance between the contacting surfaces of anvil assembly 130 and shell assembly 131.

Turning now to FIGS. 7 and 9-11, surgical instrument 100 includes a plurality of contact sensors 160, 162 placed along the length of a tissue contacting surface of each of shell assembly 131 and anvil assembly 130. Contact sensors 160, 162 are connected to the processor or CPU (see FIG. 1) and provide indication as to when an object, such as, tissue, is located between shell assembly 131 and anvil assembly 130. In operation, once initial contact is made between contact sensors 160,162 and the tissue LVDT 170 may be used to determine and/or measure the gap between shell assembly 131 and anvil assembly 130.

With continued reference to FIGS. 7 and 9-11, surgical instrument 100 may further include at least one force measuring sensor 164 provided on a surface of the head of anvil assembly 130, preferably oriented in a radially outward direction from an outer rim thereof, and at least one force measuring sensor 166 provided on an outer surface of shell assembly 131. Each force measuring sensor 164, 166 functions to measure forces acting thereon as a result of tissue pressing thereagainst, as will be discussed in greater detail below.

As seen in FIG. 7, in one embodiment, surgical instrument 100 may include a gauge 140 supported on stationary handle 118 of handle assembly 112. Each sensor 160, 162, 164, 166 may be operatively connected to gauge 140. Gauge 140 functions to display, in real time, selected operational parameters, such as, for example, tissue contact, tissue compression, tissue tension, etc.

In operation, following purse string suturing of a first tissue "T1" to anvil assembly 130 and purse string suturing of a second tissue "T2" to shell assembly 131 (as seen in FIG. 9), approximation knob 122 is rotated to approximate anvil assembly 130 towards shell assembly 131. As anvil assembly 130 and shell assembly 131 are approximated toward one another, first and second tissue "T1, T2" are extended toward one another and are tensioned. As first and second tissue "T1, T2" are tensioned, first and second tissue "T1, T2" tend to constrict around anvil assembly 130 and shell assembly 131, respectively. This constriction exerts a force on each respective force measuring sensor 164, 166. The force measured by each force measuring sensor 164, 166 may be converted, using known algorithms, to a value of tension force which is being exerted on each tissue "T1, T2".

During a surgical anastomotic procedure, the tension on first and second tissues "T1, T2" is monitored in an attempt to maintain the tension exerted thereon at or below a predetermined threshold level. For example, if the tension exerted on each tissue "T1, T2", either alone or in combination, exceeds a predetermined threshold level, said elevated tension acts on the staple line and may result in undue strains exerted on the staples and/or the staple line.

Figure 11:
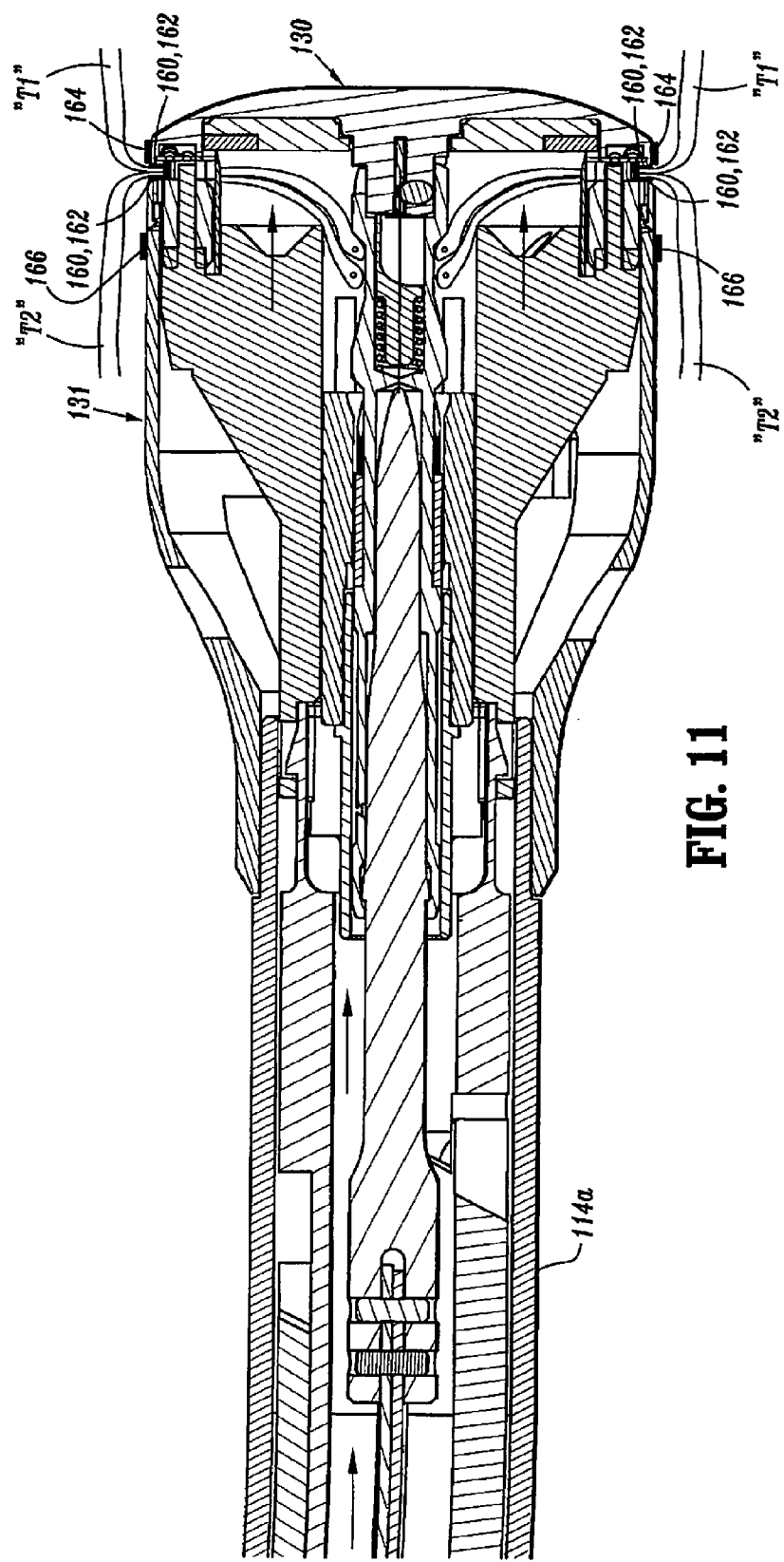
FIG. 11 is a side cross-sectional view of the distal end of the surgical instrument of FIGS. 7 and 8, shown in a third condition.
Figure 11A:
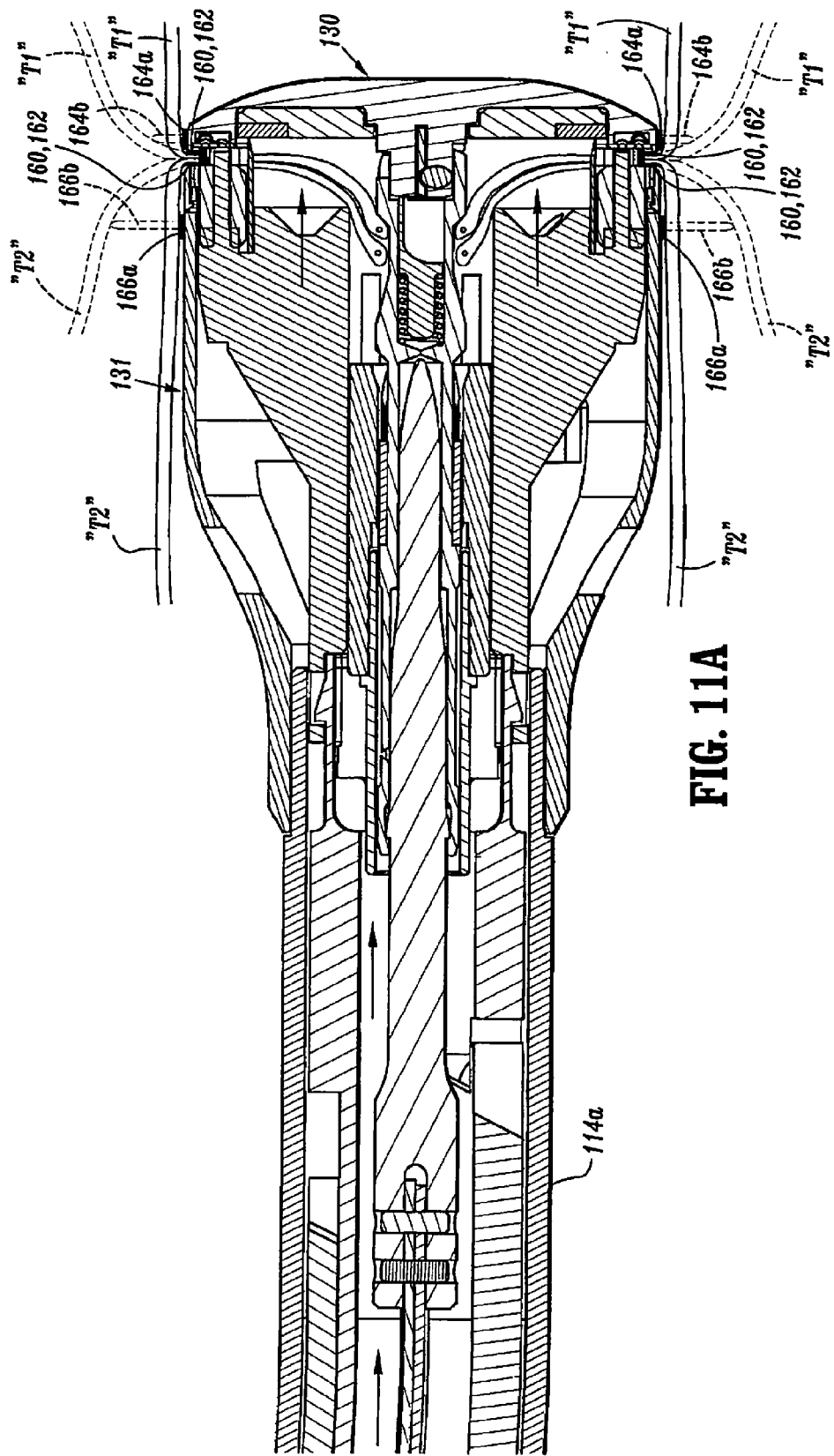
FIG. 11A is a side cross-sectional view of the distal end of the surgical instrument of FIGS. 7 and 8, illustrating the operation of a plunger sensor thereof.

In one embodiment, as seen in FIG. 11A, surgical instrument 100 includes at least one plunger sensor 164a provided on and extending radially outwardly from the head of anvil assembly 130, and at least one plunger sensor 166a provided on and extending outwardly from shell assembly 131. Each plunger sensor includes a pin 164b, 166b, respectively, slidably projecting from respective anvil assembly 130 and shell assembly 131, shown in phantom in FIG. 11A.

In operation, when a relatively low amount of tension is exerted on plunger sensors 164a, 166a, pins 164b, 166b thereof are in a substantially extended condition, as shown in phantom in FIG. 11A. However, as first and second tissue "T1, T2" are tensioned, first and second tissue "T1, T2" tend to constrict around anvil assembly 130 and shell assembly 131, respectively, thus causing pins 164b, 166b of each respective plunger sensor 164a, 166a to be pressed radially inward. The displacement of pins 164b, 166b is used to calculate and/or extrapolate the degree of tension being exerted on first and second tissue "T1, T2".

Reference may be made to U.S. patent application Ser. No. 10/528,975, filed Mar. 23, 2005, the entire content of which is incorporated herein by reference, for a more detailed discussion of the structure and operation of surgical instrument 100 and of a magnetic field sensor.

Figure 12:
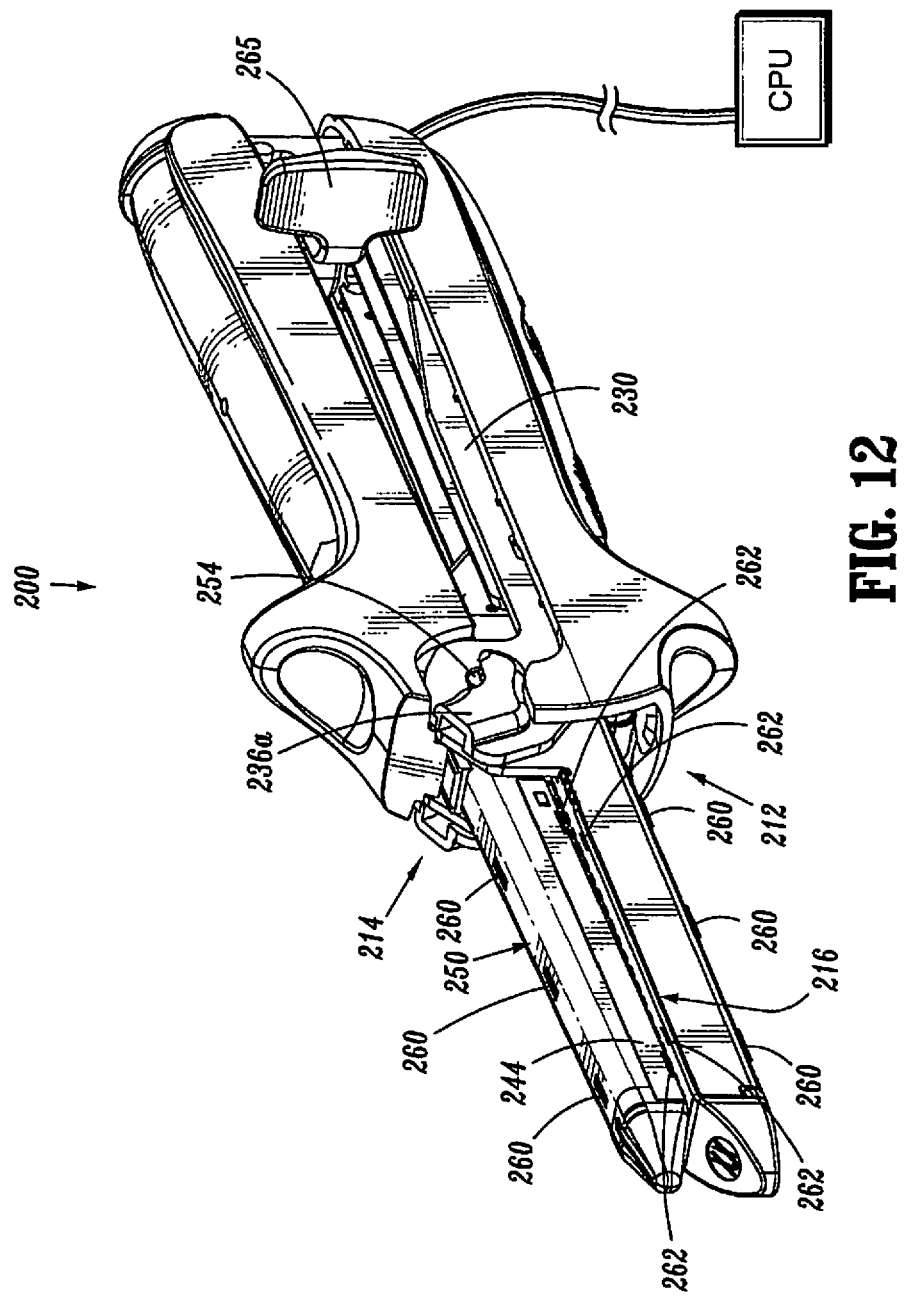
FIG. 12 is a perspective view of a surgical instrument according to yet another embodiment of the present disclosure.
Figure 13:
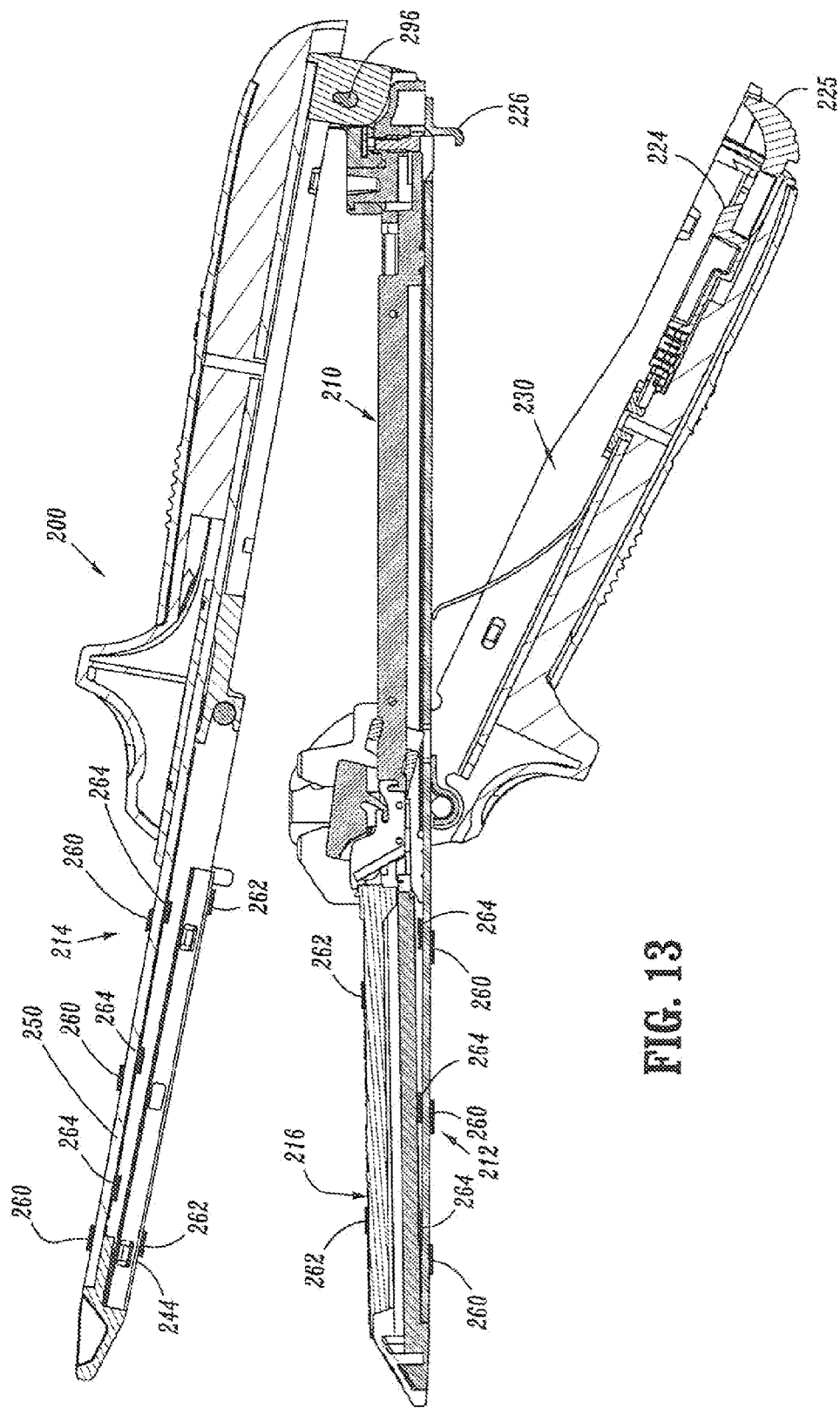
FIG. 13 is a side cross-sectional view of the surgical instrument of FIG. 12, taken along the longitudinal axis, depicting the coupling of the cartridge receiving half-section with the anvil half-section.
Figure 14:
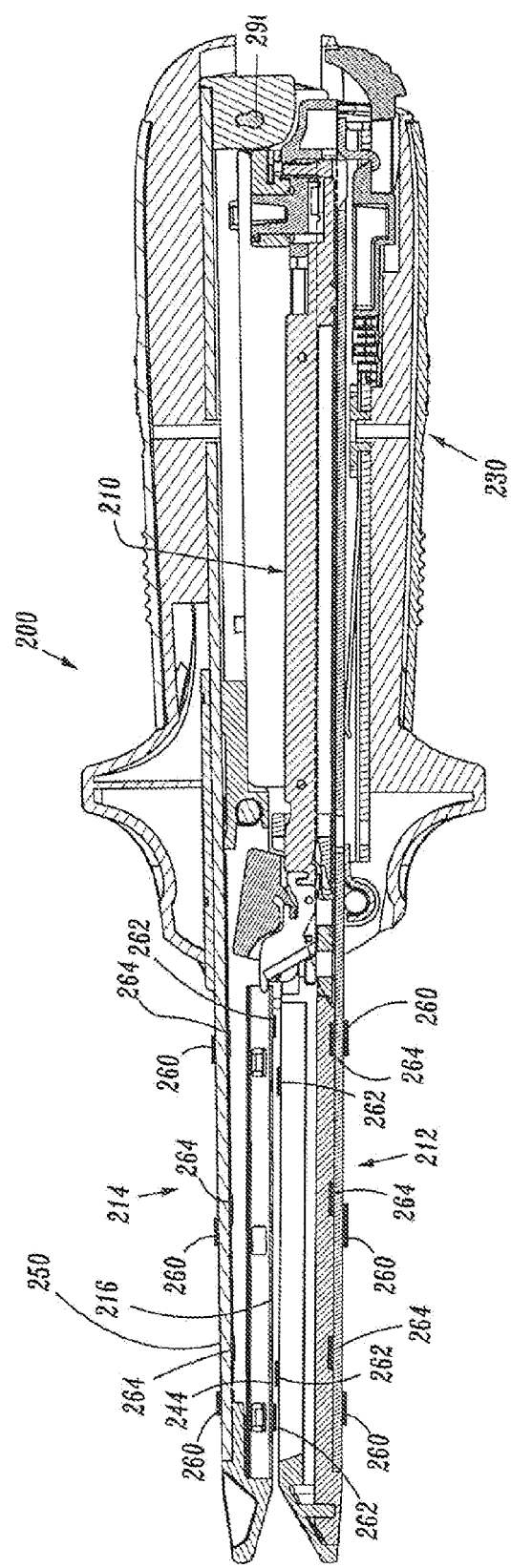
FIG. 14 is side cross-sectional view of the surgical instrument of FIGS. 12 and 13, taken along the longitudinal axis, shown in a closed pre-firing condition.

Turning now to FIGS. 12-14, a surgical instrument according to another embodiment of the present disclosure is generally designated as 200. As seen in FIGS. 12-14, surgical instrument 200 includes a cartridge receiving half-section 212, an anvil half-section 214 operatively coupled to cartridge receiving half-section 212, a cartridge assembly 216 configured and adapted to be removably mounted within a distal end of cartridge receiving half-section 212 and a firing slide 210 configured and adapted to be slidably received within cartridge receiving half-section 212. As seen in FIG. 13, with cartridge receiving half-section clamping lever 230 in an open position, a proximal end of anvil half-section 214 is slidably and pivotably receivable at a proximal end of cartridge receiving half-section 212. Surgical instrument 200 includes mounting bosses 254, projecting from anvil half-section 214, are slidably and pivotably receivable within an access channel 236a of or defined by cartridge receiving half-section clamping lever 230 in order to approximate a distal end of the cartridge receiving and anvil half-sections 212, 214.

As seen in FIG. 12, anvil half-section 214 includes an anvil half-section channel member 250 having a substantially U-shaped cross-sectional profile. Anvil half-section 214 is provided with an anvil plate 244 configured and dimensioned to be fit over anvil half-section channel member 250 of anvil half-section 214. Anvil plate 244 includes a plurality of anvil pockets formed therein (not shown), arranged in two pairs of longitudinal rows, and an anvil knife track (not shown) formed longitudinally therealong.

As seen in FIG. 12, surgical instrument 200 includes a firing lever 265 pivotably coupled thereto. Firing lever 265 is configured and adapted to provide a user with the ability to fire surgical instrument 200 from either the left or the right side thereof One method or sequence of coupling and closure of cartridge receiving half-section 212 with anvil half-section 214 is best seen in FIGS. 13 and 14. With cartridge lever 230 in an open position, as seen in FIG. 13, the proximal ends of half-section 212, 214 are approximated toward one another such that a pivot limiting pin 296 of anvil half-section 214 rests within pivot pin receiving slots of pivot plates (not shown) of cartridge receiving half-section 212. The shape of pivot limiting pin 296 limits the longitudinal angle (i.e., the angle between cartridge receiving half-section 212 and anvil half-section 214) at which anvil half-section 214 can be coupled with cartridge receiving half-section 212. With the proximal ends of half-section 212, 214 coupled to one another, the distal ends of half-section 212, 214 (or the end effector) are approximated towards one another until the mounting bosses 254, are received within access channels 236a of clamping lever 230 (see FIG. 12).

With the mounting bosses positioned within access channels 236a of cartridge lever 230, as seen in FIG. 14, the proximal end of clamping lever 230 is approximated toward cartridge receiving half-section 212 until a catch 226 of cartridge receiving half-section 212 engages a latch 224 of cartridge receiving half-section channel member 230 (see FIG. 13). By approximating clamping lever 230 toward cartridge receiving half-section 212, the mounting bosses are advanced through access channels 236a thereby completing the approximation of cartridge receiving half-section 212 with anvil half-section 214.

Reference may be made to U.S. patent application Ser. No. 10/508,191, filed Sep. 17, 2004, the entire content of which is incorporated herein by reference, for a more detailed discussion of the structure and operation of surgical instrument 200.

As seen in FIGS. 12-14, surgical instrument 200 includes gap sensing and/or measuring elements (e.g., magneto-resistive elements) 260 placed along at least a portion of the length of the distal ends of each of the cartridge receiving half-section 212 and the anvil half-section 214. Gap measuring elements 260 may be placed along an outer surface and/or along an inner surface of each of the cartridge receiving half-section 212 and the anvil half-section 214.

Surgical instrument 200 further includes contact sensing elements 262 placed along the tissue contacting surfaces of each of the anvil plate 244 and the cartridge assembly 216. In this manner, as surgical instrument 200 is being clamped onto target tissue, the contact sensing elements 262 will provide the user with an indication (i.e., audio, visual, tactile, etc.) as to when the target tissue is initially brought into contact with the tissue contacting surfaces of each of the anvil plate 244 and the cartridge assembly 216. In one embodiment, it is desirable to determine when the tissue contacts solely a distal end of anvil plate 244 and/or cartridge assembly 216.

As seen in FIGS. 13 and 14, surgical instrument 200 further includes force sensing and/or measuring elements 264 (e.g., strain gauges, load cells, etc.) placed along at least a portion of the length of the distal ends of each of the cartridge receiving half-section 212 and the anvil half-section 214. In this manner, in operation, force sensing and/or measuring elements 264 are capable of transmitting measurements of the clamping forces being applied to the target tissue by the distal ends of the cartridge receiving half-section 212 and the anvil half-section 214.

Figure 15:
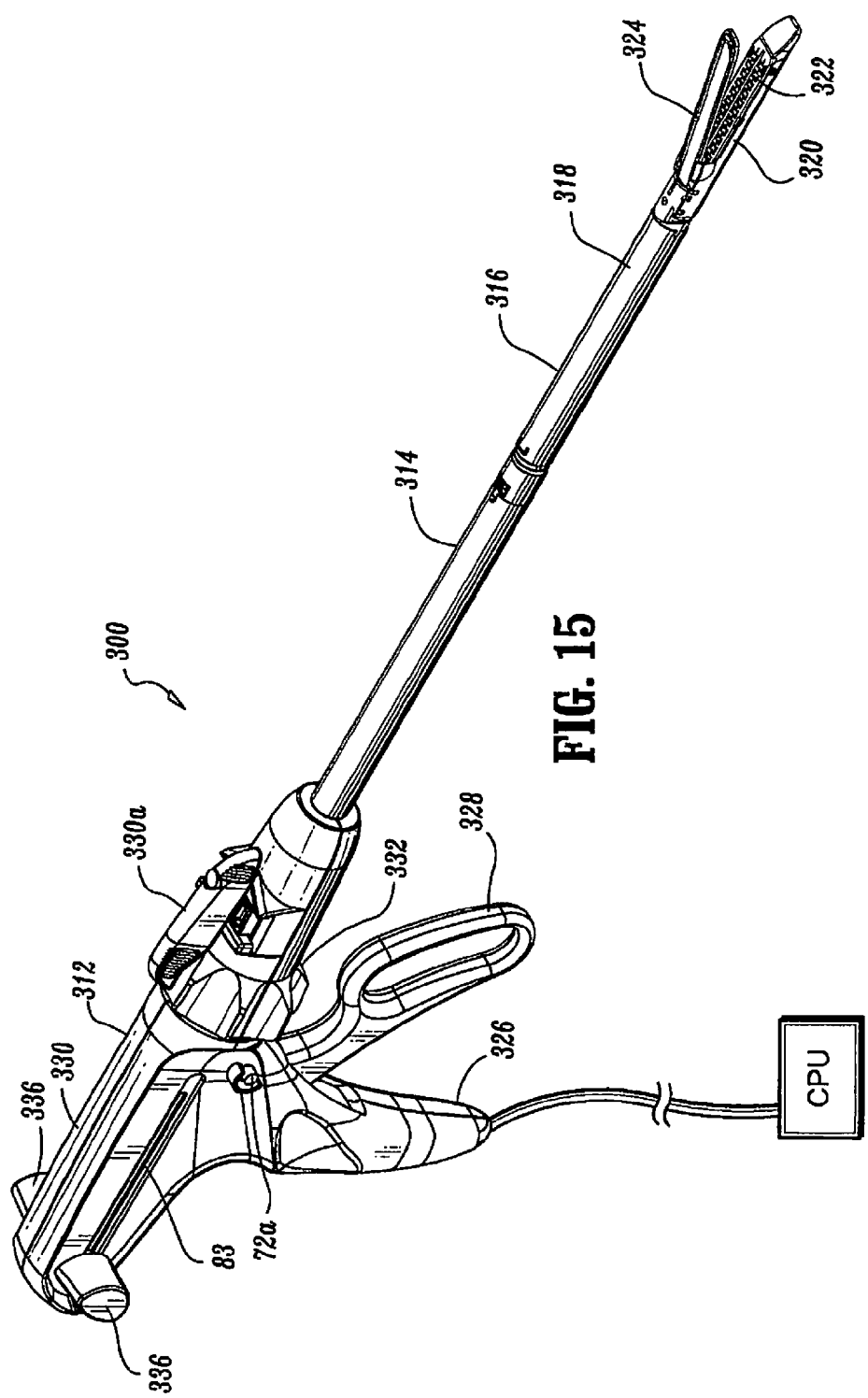
FIG. 15 is a perspective view of a surgical instrument according to yet another embodiment of the present disclosure.
Figure 16:
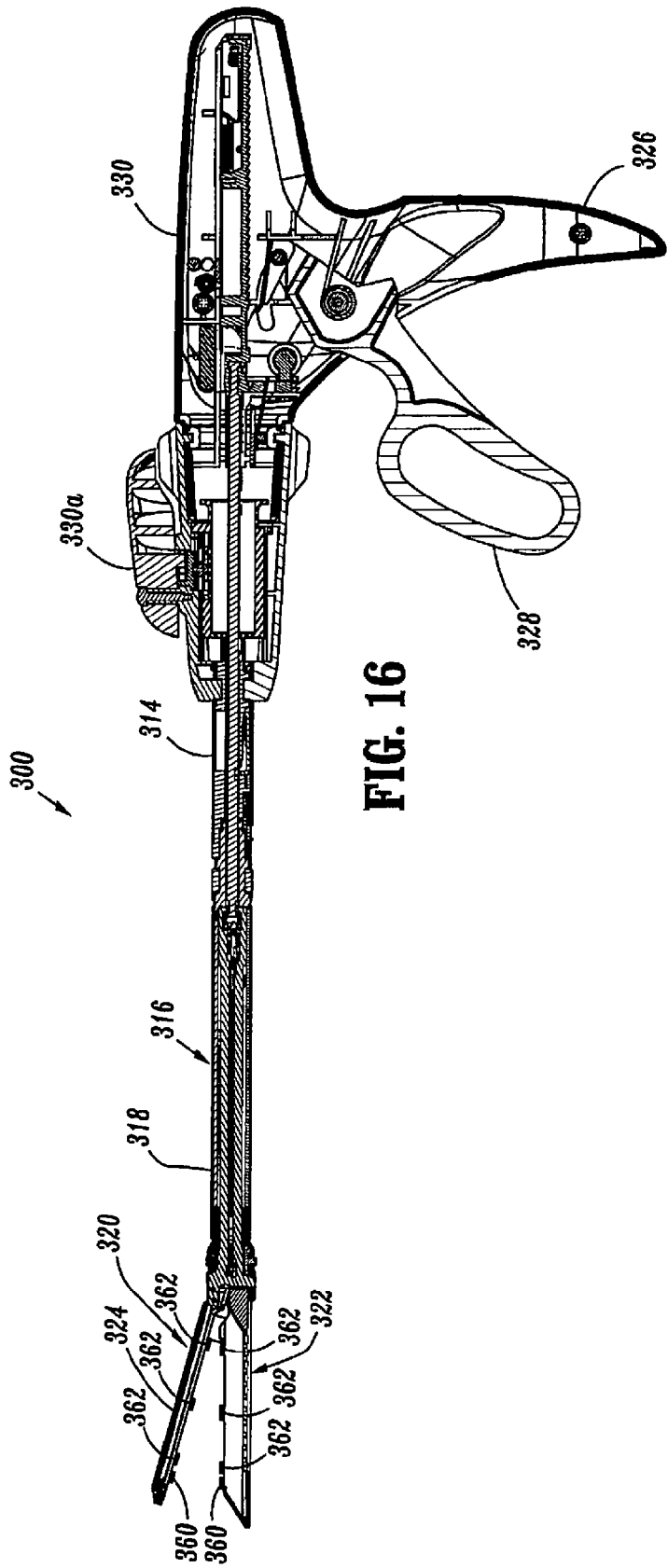
FIG. 16 is a side, cross-sectional view of the surgical instrument of FIG. 15, shown in a first, unapproximated condition.

Turning now to FIGS. 15-19, a surgical instrument according to another embodiment of the present disclosure is generally designated as 300. As seen in FIGS. 15 and 16, surgical instrument 300 includes a handle assembly 312 and an elongated body 314. As illustrated in FIGS. 15 and 16, the length of elongated body 314 may vary to suit a particular surgical procedure. A disposable loading unit or DLU 316 is releasably secured to a distal end of elongated body 314. DLU 316 includes a proximal body portion 318, which forms an extension of elongated body 314, and a distal tool assembly or end effector 320 including a first member or cartridge assembly 322 and a second member or anvil assembly 324. Tool assembly 320 is pivotably connected to body 318 about an axis substantially perpendicular to the longitudinal axis of elongated body 314. Cartridge assembly 322 houses a plurality of staples. Anvil assembly 324 is movable in relation to cartridge assembly 322 between an open position spaced from cartridge assembly 322 and an approximated or clamped position in juxtaposed alignment with cartridge assembly 322. The staples may be housed in cartridge assembly 322 to apply linear rows of staples having a length measuring from about 30 mm to about 60 mm, although other staple configurations and lengths are envisioned.

Handle assembly 312 includes a stationary handle member 326, a movable handle or trigger 328 and a barrel portion 330. A rotatable member 332 is rotatably mounted to the forward end of barrel portion 330 and secured to elongated body 314 to facilitate rotation of elongated body 314 in relation to handle assembly 312. An articulation lever 330a is supported on a distal portion of barrel portion 330 and is operable, in a manner to be described hereafter, to effect articulation of tool assembly 320 with respect to body portion 318 of DLU 316. A pair of return knobs 336 are movably supported along barrel portion 330 to effect movement of surgical instrument 300 from an advanced position to a retracted position.

Figure 19:
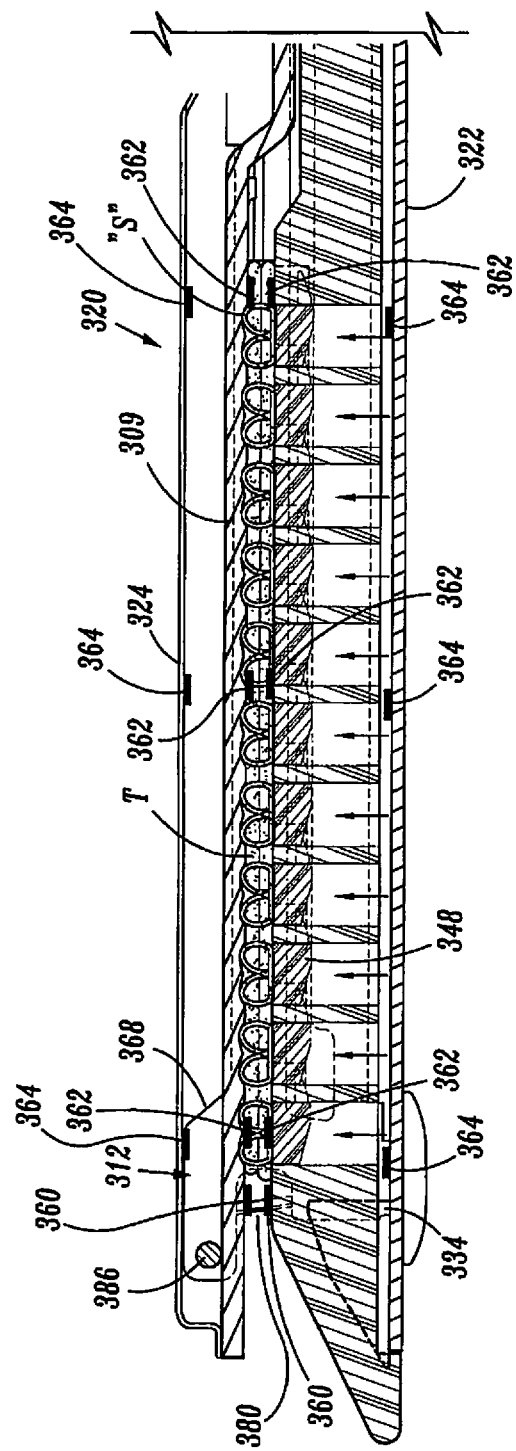
FIG. 19 in an enlarged, side cross-sectional view of a tool assembly of the surgical instrument of FIGS. 15 and 16, shown after completion of a firing stroke.

As seen in FIGS. 17-19, surgical instrument 300 includes an axial drive assembly 312 including a distal working head 368. A distal end of working head 368 supports a cylindrical cam roller 386. Cam roller 386 is dimensioned and configured to engage a cam surface 309 of anvil assembly 324 to clamp anvil assembly 324 against body tissue "T".

In operation, to approximate the cartridge and anvil assemblies 322 and 324, movable handle 328 is moved toward stationary handle 326, through an actuation stroke. Subsequent movement of movable handle 328 through the actuation stroke effects advancement of an actuation shaft and a firing rod (not shown). As the actuation shaft is advanced, so to is the firing rod.

The firing rod is connected at its distal end to axial drive assembly 312 such that advancement of the firing rod effects advancement of drive assembly 312. As drive assembly 312 is advanced, cam roller 386 moves into engagement with cam surface 309 of anvil assembly 324 (see FIGS. 17 and 18) to urge anvil assembly 324 toward cartridge assembly 322, thereby approximating cartridge and anvil assemblies 322 and 324 and clamping tissue "T" therebetween.

To fire surgical instrument 300, movable handle 328 is moved through a second actuation stroke to further advance the actuation shaft and the firing rod distally. As the firing rod is advanced distally, drive assembly 312 is advanced distally to advance actuation sled 334 through staple cartridge assembly 322 to simultaneously sever tissue with knife 380 (see FIGS. 17-19) and drive pushers 348 to sequentially eject staples "S" from cartridge assembly 322.

Surgical instrument 300 is adapted to receive DLU's having staple cartridges with staples in linear rows having a length of from about 30 mm to about 60 mm. For example, each actuation stroke of movable handle 328 during firing of surgical instrument 300 may advance the actuation shaft approximately 15 mm, although other lengths are envisioned. Accordingly, to fire a cartridge assembly having a 45 mm row of staples, movable handle 328 must be moved through three actuation strokes after the approximating or clamping stroke of movable handle 328.

Reference may be made to U.S. patent application Ser. No. 10/490,790, filed Mar. 24, 2004, the entire content of which is incorporated herein by reference, for a more detailed discussion of the structure and operation of surgical instrument 300.

As best seen in FIGS. 16-18, surgical instrument 300 includes gap sensing and/or measuring elements (e.g., magneto-resistive elements) 360 placed along at least a portion of the length of the distal ends of each of the cartridge assembly 322 and the anvil assembly 324. Gap measuring elements 360 may be placed along an outer surface and/or along an inner surface of each of the cartridge assembly 322 and the anvil assembly 324.

Surgical instrument 300 further includes contact sensing elements 362 placed along the tissue contacting surfaces of each of the anvil assembly 324 and the cartridge assembly 322. In this manner, as surgical instrument 300 is being clamped onto target tissue "T", the contact sensing elements 362 will provide the user with an indication (i.e., audio, visual, tactile, etc.) as to when the target tissue is initially brought into contact with the tissue contacting surfaces of each of the anvil assembly 324 and the cartridge assembly 322.

As seen in FIGS. 17 and 18, surgical instrument 300 further includes force sensing and/or measuring elements 364 (e.g., strain gauges, load cells, etc.) placed along at least a portion of the length of the distal ends of each of the cartridge assembly 322 and the anvil assembly 324. In this manner, in operation, force sensing and/or measuring elements 364 are capable of transmitting measurements of the clamping forces being applied to the target tissue by the distal ends of the cartridge assembly 322 and the anvil assembly 324. Reference may be made to U.S. application Ser. No. 11/409,154, filed on Apr. 21, 2006, the entire content of which is incorporated herein by reference, for a more detailed discussion of force sensing and/or measuring elements, such as load cells and/or strain gauges.

In an embodiment, capacitive elements may be used to determine the gap between the jaw members of the surgical instrument. For example, a plate may be mounted on, or near, each side of the jaw members such that movement of the jaw members changes the gap between the plates of the capacitive element or the amount of shared area, or overlap, of the plates of the capacitive element. By applying a voltage between the plates a capacitor and an electric field may be formed between the plates. The potential applied to the plates, the gap between the plates and the amount of overlap of the plates would thus enable the capacitor to store energy and to determine the strength and size of the electric field. Motion of the jaw members may be translated into a change in capacitance and a change in the electric field. Either or both may be measured and used to determine the separation distance or movement of the jaw members.

In another embodiment, any of the aforementioned surgical instruments may include and/or incorporate the use of electromagnetic induction sensors in order to determine the gap. Electromagnetic induction sensors may be used to detect changes in sensor coil impedance resulting from a change in distance between the sensor coil and a conductive target material. For example, a coil driven by an alternating current may generate an oscillating magnetic field that, in turn, induces eddy currents in a target metallic object. The eddy currents move in a direction opposite the current of the coil thereby reducing magnetic flux in the coil and its inductance. Eddy currents also dissipate energy increasing the coil's resistance. In use, resistance increases and inductance decreases as the target approaches the coil. These changes in resistance and inductance are proportional to the distance and are the basis of position sensing when using electromagnetic induction sensors.

In still another embodiment, any of the aforementioned surgical instruments may include and/or incorporate the use of inductive sensors, such as linear variable differential transformers (LVDT's), to transduce motion into an electrical signal in order to determine the gap. Movement of the elements of surgical instrument including inductive sensors, relative to each other, alters an overall inductance or inductive coupling. These changes in inductance or inductive coupling may be detected and are the basis for LVDT position sensing.

In yet another embodiment, any of the aforementioned surgical instruments may include and/or incorporate the use of thin film giant magnetoresistive (GMR) materials that are placed adjacent to a source for producing a magnetic field. For example, the GMR and the source for producing the magnetic field may be placed on respective ones of the jaw members of the surgical instrument. Accordingly, the distance from the GMR material to the source for producing the magnetic field would vary with changes in the size of the gap between the jaw members. A thin film GMR material may include two layers of magnetic material. The electrical conductivity of each layer is dependent upon the magnetic alignment of the individual layers and on the spin of the individual electrons. A layer with a particular magnetic alignment will only allow electrons of a particular spin to pass. If the layers are not in alignment, electrons with a particular spin pass through one layer, but not the other, so the overall resistance is high. If the layers are in magnetic alignment, which occurs when GMR film is placed in a magnetic field, both layers are permeable to electrons with the same spin and resistance therethrough is decreased. The layers electrical conductivity deposited on silicone substrates can be configured as resistors in a variety of configurations, the most common of which is the Wheatstone bridge. The distance from the GMR to the source for producing the magnetic field is calculated based on the relationship between field strength and distance.

In an embodiment, any of the aforementioned surgical instruments may include and/or incorporate the use of Hall effect sensors to determine the size of the gap between the jaw members. Hall effect sensors are sheets of semiconductor material across which a constant voltage is applied and which conduct a constant bias current. The voltage difference across the sheet on the axis perpendicular to the constant applied voltage is proportional to the strength of the magnetic field the sheet is exposed to. The distance from the sensor to the magnet is determined knowing the relationship between the field strength and distance.

In another embodiment, the size of the gap between the jaw members of any of the aforementioned surgical instruments may be determined by using optical based sensors. One type of optical based sensor includes a diffuser sensor, which typically includes a light emitter and a light receiver that are placed in juxtaposed relation to one another. The light receiver measures the intensity of reflected light from the target tissue. The intensity of reflected light is related to the distance between the light emitter and the target tissue, and such distance translates to the stapler gap distance.

Another type of optical sensor includes a time-of-flight sensor. Time-of-flight sensors measure distance by dividing the velocity of light by the time it takes for emitted light and/or the reflected light to be detected by a receiver. A further type of optical sensor utilizes triangulation techniques. Triangulation is a measurement scheme by which a laser projects a collimated beam that reflects off a target and passes through a lens that focuses the reflected beam onto a receiving element. Changes in distance between the sensor and target result in changes of the angle of the returning light and consequent change in the position of the beam on the receiving array. The distance is determined by the position of the beam on the receiving array.

In yet another embodiment, the size of the gap between the jaw members of any of the aforementioned surgical instruments may be determined by utilizing ultrasonic sensors that measure distance by reflecting a known velocity of a soundwave by one-half the time required for an emitted sound to reflect off a target and to return to the sensor. These ultrasonic sensors may be incorporated into each jaw member of the surgical instrument.

In still another embodiment, the linear motion of the jaw members of any one of the aforementioned surgical instruments may be coupled to an adjustable variable resistor, or potentiometer ("POT"). A POT typically includes a resistive element attached to a circuit via two fixed contacts at each end of the resistive element and a third contact, or wiper that can slide between each end. The sliding contact divides the POT into two resistors and the voltage across the two fixed contacts is divided between each fixed contact and the wiper. The POT can be configured such that the linear motion is coupled to the position of the wiper such that the output voltage is directly related to a linear position thereof.

Figure 20:
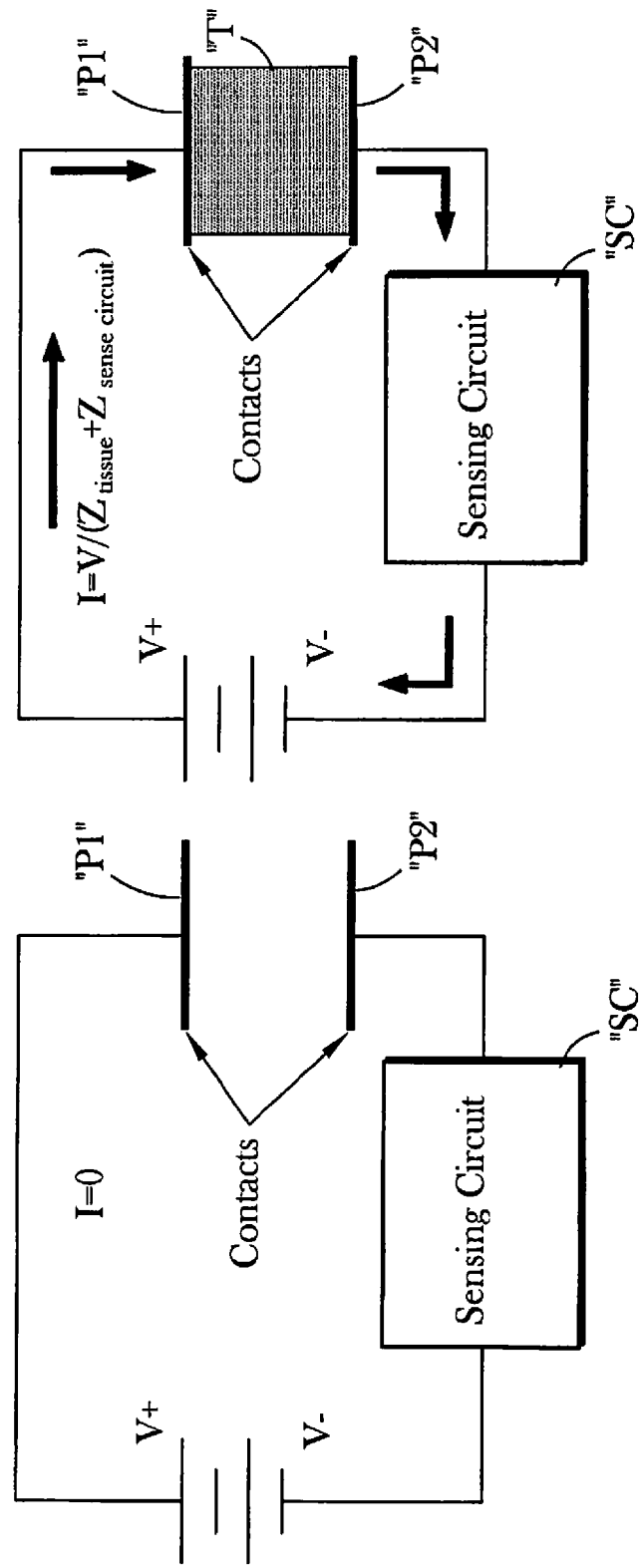
FIG. 20 is a schematic illustration of a tissue contact circuit showing the completion of the circuit upon contact with tissue a pair of spaced apart contact plates.

As described supra, tissue contact or pressure sensors determine when the jaw members initially come into contact with the tissue "T". This enables a surgeon to determine the initial thickness of the tissue "T" and/or the thickness of the tissue "T" prior to clamping. In any of the surgical instrument embodiments described above, as seen in FIG. 20, contact of the jaw members with tissue "T" closes a sensing circuit "SC" that is otherwise open, by establishing contacting with a pair of opposed plates "P1, P2" provided on the jaw members. The contact sensors may also include sensitive force transducers that determine the amount of force being applied to the sensor, which may be assumed to be the same amount of force being applied to the tissue "T". Such force being applied to the tissue, may then be translated into an amount of tissue compression. The force sensors measure the amount of compression a tissue is under and provide a surgeon with information about the force applied to the tissue "T". Excessive tissue compression may have a negative impact on the tissue "T" being operated on. For example, excessive compression of tissue "T" may result in tissue necrosis and, in certain procedures, staple line failure. Information regarding the pressure being applied to tissue "T" enables a surgeon to better determine that excessive pressure is not being applied to tissue "T".

Any of the contact sensors disclosed herein may include, and are not limited to, electrical contacts placed on an inner surface of a jaw which, when in contact with tissue, close a sensing circuit that is otherwise open. The contact sensors may also include sensitive force transducers that detect when the tissue being clamped first resists compression. Force transducers may include, and are not limited to, piezoelectric elements, piezoresistive elements, metal film or semiconductor strain gauges, inductive pressure sensors, capacitive pressure sensors, and potentiometric pressure transducers that use bourbon tubes, capsules or bellows to drive a wiper arm on a resistive element.

In an embodiment, any one of the aforementioned surgical instruments may include one or more piezoelectric elements to detect a change in pressure occurring on the jaw members. Piezoelectric elements are bi-directional transducers which convert stress into an electrical potential. Elements may consist of metallized quartz or ceramics. In operation, when stress is applied to the crystals there is a change in the charge distribution of the material resulting in a generation of voltage across the material. Piezoelectric elements may be used to indicate when any one or both of the jaw members makes contact with the tissue "T" and the amount of pressure exerted on the tissue "T" after contact is established.

In an embodiment, any one of the aforementioned surgical instruments may include or be provided with one or more metallic strain gauges placed within or upon a portion of the body thereof. Metallic strain gauges operate on the principle that the resistance of the material depends upon length, width and thickness. Accordingly, when the material of the metallic strain gauge undergoes strain the resistance of the material changes. Thus, a resistor made of this material incorporated into a circuit will convert strain to a change in an electrical signal. Desirably, the strain gauge may be placed on the surgical instruments such that pressure applied to the tissue effects the strain gauge.

Alternatively, in another embodiment, one or more semiconductor strain gauges may be used in a similar manner as the metallic strain gauge described above, although the mode of transduction differs. In operation, when a crystal lattice structure of the semiconductor strain gauge is deformed, as a result of an applied stress, the resistance of the material changes. This phenomenon is referred to as the piezoresistive effect.

In yet another embodiment, any one of the aforementioned surgical instruments may include or be provided with one or more inductive pressure sensors to transduce pressure or force into motion of inductive elements relative to each other. This motion of the inductive elements relative to one another alters the overall inductance or inductive coupling. Capacitive pressure transducers similarly transduce pressure or force into motion of capacitive elements relative to each other altering the overall capacitance.

In still another embodiment, any one of the aforementioned surgical instruments may include or be provided with one or more capacitive pressure transducers to transduce pressure or force into motion of capacitive elements relative to each other altering an overall capacitance.

In an embodiment, any one of the aforementioned surgical instruments may include or be provided with one or more mechanical pressure transducers to transduce pressure or force into motion. In use, a motion of a mechanical element is used to deflect a pointer or dial on a gauge. This movement of the pointer or dial may be representative of the pressure or force applied to the tissue "T". Examples of mechanical elements include and are not limited to bourbon tubes, capsules or bellows. By way of example, mechanical elements may be coupled with other measuring and/or sensing elements, such as a potentiometer pressure transducer. In this example the mechanical element is coupled with a wiper on the variable resistor. In use, pressure or force may be transduced into mechanical motion which deflects the wiper on the potentiometer thus changing the resistance to reflect the applied pressure or force.

The combination of the above embodiments, in particular the combination of the gap and tissue contact sensors, provides the surgeon with feedback information and/or real-time information regarding the condition of the operative site and/or target tissue "T". For example, information regarding the initial thickness of the tissue "T" may guide the surgeon in selecting an appropriate staple size, information regarding the clamped thickness of the tissue "T" may let the surgeon know if the selected staple will form properly, information relating to the initial thickness and clamped thickness of the tissue "T" may be used to determine the amount of compression or strain on the tissue "T", and information relating to the strain on the tissue "T" may be used this strain to avoid compressing tissue to excessive strain values and/or stapling into tissue that has undergone excessive strain.

Additionally, force sensors may be used to provide the surgeon with the amount of pressure applied to the tissue. The surgeon may use this information to avoid applying excessive pressure on the tissue "T" or stapling into tissue "T" which has experienced excessive strain.

With reference to FIGS. 1 and 4-6A, in addition to contact sensors 60, surgical instrument 10 may include strain gauges 62 placed along the length of the tissue contact surface of each of cartridge assembly 20 and anvil assembly 22.

As seen in FIGS. 1, 7, 12 and 15, any of the aforementioned surgical instruments may be selectively electrically connected to a central processing unit (CPU), an e-motor (electronic motor) or the like for monitoring, controlling, processing and/or storing information observed, measured, sensed and/or transmitted from any of the elements of components of the surgical instruments prior, during and/or after the surgical procedure.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical instrument for operating on tissue, comprising:
   an end effector including a first tissue engaging member and a second tissue engaging member in juxtaposed relation to the first tissue engaging member, at least one of the first and second tissue engaging members movable from a first configuration for positioning tissue therebetween to second configuration for compressing tissue; and
   a gap determination element disposed on the surgical instrument and configured to measure a gap distance between the first tissue engaging member and the second tissue engaging member;
   at least one tissue contact determining element positioned on each of the first and second tissue engaging members and contactable with tissue positioned therebetween; and a processor in operative communication with the gap determination element and each of the at least one tissue contact determining element, the processor configured to measure voltages generated by the gap determination element and receive signals provided by each of the at least one tissue contact determining element for determining when tissue is sufficiently compressed.

2. The surgical instrument according to claim 1, wherein the gap determination element generates a first voltage corresponding to a first condition of the gap determination element, and generates a second voltage corresponding to a second condition of the gap determination element.

3. The surgical instrument according to claim 2, wherein the first condition of the gap determination element is indicative of the first and second tissue engaging surfaces being in a spaced-apart position and the second configuration of the gap determination element is indicative of the first and second tissue engaging surfaces being in an approximated position.

4. The surgical instrument according to claim 1, wherein the gap determination element is remotely located from the end effector assembly and movable relative thereto.

5. The surgical instrument according to claim 1, wherein the tissue contact determining elements are positioned on a respective tissue contacting surface of the first tissue engaging member and the second tissue engaging member.

6. The surgical instrument according to claim 1, further including a sensing circuit in operable communication with the processor and configured to determine when tissue is positioned between the first tissue engaging member and the second tissue engaging member.

7. The surgical instrument according to claim 6, wherein the tissue contact determining elements are in the form of a pair of electrical contacts operably disposed on a respective one of the first and second tissue engaging members.

8. The surgical instrument according to claim 7, wherein the sensing circuit transmits a signal to the processor when a tissue is:
   positioned between the first and second tissue engaging elements, and
   contacts the electrical contacts.

9. The surgical instrument according to claim 8, wherein the signal transmitted to the processor is indicative of tissue thickness.

10. The surgical instrument according to claim 9, wherein the processor is configured to activate a signal when at least one of a compression force and strain on the tissue achieves a predetermined level of compression or strain.

11. The surgical instrument according to claim 10, wherein the predetermined level of compression or strain is a percentage of the initial tissue thickness.

12. The surgical instrument according to claim 10, wherein the predetermined level of compression or strain on the tissue is maintained in a data look-up table.

13. The surgical instrument according to claim 12, wherein the data look-up table includes predetermined levels of compression or strain for numerous tissue types.

14. The surgical instrument according to claim 1, wherein the gap determination element is selected from the group consisting of a slide potentiometer, a rotational potentiometer, a linear variable differential transformer, a magneto-resistive element, capacitive elements, electromagnetic induction sensors, Hall effect sensors, and optical based sensors.

15. The surgical instrument according to claim 1, wherein the tissue contact determining elements are selected from the group consisting of pressure sensors, force transducers, piezoelectric elements, piezoresistive elements, metal film strain gauges, semiconductor strain gauges, inductive pressure sensors, capacitive pressure sensors, and potentiometric pressure transducers.

16. The surgical instrument according to claim 1, wherein the surgical instrument is a stapler.

17. The surgical instrument according to claim 1, further comprising at least one first force measuring sensor provided on a surface of the first tissue engaging member, wherein the first force measuring sensor is oriented in an outward direction from an outer surface thereof, and at least one second force measuring sensor provided on the second tissue engaging member, wherein each second force measuring sensor is oriented in an outward direction from an outer surface thereof.

18. The surgical instrument according to claim 17, wherein each of the first and second force measuring sensors functions to measure forces acting thereon as a result of tissue pressing thereagainst.

19. The surgical instrument according to claim 18, further comprising a gauge operatively connected to each of the first and second force measuring sensors.

* * * * *